(12) United States Patent
Monforte et al.

(10) Patent No.: US 6,566,055 B1
(45) Date of Patent: *May 20, 2003

(54) METHODS OF PREPARING NUCLEIC ACIDS FOR MASS SPECTROMETRIC ANALYSIS

(75) Inventors: Joseph A. Monforte, Berkeley, CA (US); Thomas A. Shaler, Fremont, CA (US); Yuping Tan, Fremont, CA (US); Christopher H. Becker, Menlo Part, CA (US)

(73) Assignee: Sequenom, Inc., San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/089,730

(22) Filed: Jun. 3, 1998

Related U.S. Application Data

(60) Division of application No. 08/759,993, filed on Dec. 2, 1996, now Pat. No. 5,965,363, and a continuation-in-part of application No. 08/715,582, filed on Sep. 19, 1996, now abandoned.

(51) Int. Cl.[7] ............... C12Q 1/68; C12P 19/34; H01H 21/44; C07H 21/04
(52) U.S. Cl. ............ 435/6; 435/91.1; 435/91.2; 250/281
(58) Field of Search ............. 435/86, 91.2, 6; 250/281

(56) References Cited

U.S. PATENT DOCUMENTS

| 3,776,700 A | 12/1973 | Gallant ............ 422/65 |
| 3,807,235 A | 4/1974 | Lefkovitz .......... 73/863.32 |

(List continued on next page.)

FOREIGN PATENT DOCUMENTS

| DE | 4431174 A1 | 3/1996 |
| DE | 19617011 | 4/1996 |
| DE | 4438630 A1 | 5/1996 |
| DE | 19618032 | 5/1996 |
| DE | 19628178 | 7/1996 |
| DE | 19754978 | 12/1997 |
| EP | 0593789 A1 | 4/1994 |
| GB | 2017105 | 3/1979 |
| GB | 2260811 A | 4/1993 |
| GB | 2312782 | 11/1997 |
| GB | 2332273 | 6/1999 |
| JP | 4178359 | 6/1992 |
| WO | 8903432 | 4/1989 |
| WO | 8906700 | 7/1989 |
| WO | 8912624 | 12/1989 |
| WO | 9001564 | 2/1990 |
| WO | WO 91/11533 | 8/1991 |
| WO | WO 93/08305 | 10/1992 |
| WO | 9309668 | 5/1993 |
| WO | 9323563 | 11/1993 |
| WO | WO 94/16090 | 1/1994 |
| WO | WO 94/11530 | 5/1994 |
| WO | WO 94/16101 | 7/1994 |
| WO | 9421822 | 9/1994 |
| WO | 9428418 | 12/1994 |
| WO | 9513381 | 5/1995 |
| WO | 9513538 | 5/1995 |
| WO | 9515400 | 6/1995 |
| WO | WO 95/04160 | 9/1995 |
| WO | 9610648 | 4/1996 |
| WO | WO 96/14406 | * 5/1996 |
| WO | 9615262 | 5/1996 |
| WO | 9617080 | 6/1996 |
| WO | WO 96/29431 | 9/1996 |
| WO | 9630545 | 10/1996 |
| WO | 9632504 | 10/1996 |
| WO | WO 96/37630 | 11/1996 |
| WO | 9708306 | 3/1997 |
| WO | WO 97/33000 | 3/1997 |
| WO | WO 97/27327 | 7/1997 |
| WO | 9737041 | 10/1997 |
| WO | 9740462 | 10/1997 |
| WO | 9742348 | 11/1997 |
| WO | 9743617 | 11/1997 |
| WO | 9803257 | 1/1998 |
| WO | 9812734 | 3/1998 |
| WO | 9820019 | 5/1998 |
| WO | 9820020 | 5/1998 |
| WO | 9820166 | 5/1998 |
| WO | 9823284 | 6/1998 |
| WO | 9824935 | 6/1998 |
| WO | 9826095 | 6/1998 |
| WO | 9833052 | 7/1998 |
| WO | 9833808 | 8/1998 |
| WO | 9835609 | 8/1998 |
| WO | 9905323 | 2/1999 |
| WO | 9912040 | 3/1999 |
| WO | 9931278 | 6/1999 |
| WO | 9957318 | 11/1999 |
| WO | 0051053 | 8/2000 |
| WO | 0056446 | 9/2000 |
| WO | 0060361 | 10/2000 |

OTHER PUBLICATIONS

Adler et al., "Cell Membrane Coating with Glutaraldehyde: Application to a Versatile Solid–Phase Assay for Thyroid Membrane Proteins and Molecules Interacting with Thyroid Membranes", *Anal. Biochem.*, 148:320–327 (1985).

Batista–Viera et al., "A new method for reversible immobilization of thiol biomolecules bsed on solid–phase bound thiosulfonate gorups," *App. Biochem and Biotech*, 31:175–195 (1991).

(List continued on next page.)

*Primary Examiner*—Michael Borin
(74) *Attorney, Agent, or Firm*—Stephanie L. Seidman; Heller Ehrman White & McAuliffe, LLP

(57) ABSTRACT

This invention relates to methods for screening nucleic acids for polymorphisms by analyzing amplified target nucleic acids using mass spectrometric techniques and to procedures for improving mass resolution and mass accuracy of these methods of detecting polymorphisms.

48 Claims, 15 Drawing Sheets

U.S. PATENT DOCUMENTS

| | | | | |
|---|---|---|---|---|
| 4,139,346 | A | 2/1979 | Rabbani | 422/56 |
| 4,461,328 | A | 7/1984 | Kenney | 422/100 |
| 4,554,839 | A | 11/1985 | Hewett et al. | 73/864.16 |
| 4,604,363 | A | 8/1986 | Newhouse et al. | 436/177 |
| 4,775,619 | A | 10/1988 | Urdea | |
| 4,779,467 | A | 10/1988 | Rainin et al. | 73/863.32 |
| 4,806,546 | A | 2/1989 | Carrico et al. | 536/27 |
| 4,877,745 | A | 10/1989 | Hayes et al. | 436/166 |
| 4,882,127 | A | 11/1989 | Rosenthal et al. | 422/50 |
| 4,925,629 | A | 5/1990 | Schramm | 422/82.05 |
| 4,935,357 | A | 6/1990 | Szybalski | |
| 4,952,518 | A | 8/1990 | Johnson et al. | 436/518 |
| 5,000,921 | A | 3/1991 | Hanaway et al. | 422/100 |
| 5,003,059 | A | 3/1991 | Brennan | |
| 5,059,654 | A | 10/1991 | Hou et al. | 525/54.1 |
| 5,064,754 | A | 11/1991 | Mills | |
| 5,075,217 | A | 12/1991 | Weber | |
| 5,108,703 | A | 4/1992 | Pfost et al. | 422/65 |
| 5,143,451 | A | 9/1992 | Millgard | 374/25 |
| 5,143,854 | A | 9/1992 | Pirrung et al. | 436/518 |
| 5,149,625 | A | 9/1992 | Church | 435/6 |
| 5,221,518 | A | 6/1993 | Mills | 422/62 |
| 5,262,128 | A | 11/1993 | Leighton et al. | 422/100 |
| 5,288,644 | A | 2/1994 | Beavis et al. | |
| 5,338,688 | A | 8/1994 | Deeg et al. | 436/180 |
| 5,350,676 | A | 9/1994 | Oberhardt et al. | 435/13 |
| 5,364,759 | A | 11/1994 | Caskey et al. | |
| 5,364,760 | A | 11/1994 | Chu et al. | 435/6 |
| 5,369,004 | A | 11/1994 | Polymeroulos et al. | |
| 5,378,602 | A | 1/1995 | Polymeroulos et al. | |
| 5,403,711 | A | 4/1995 | Walder et al. | 435/6 |
| 5,436,143 | A | * 7/1995 | Hyman | 435/91.2 |
| 5,439,649 | A | 8/1995 | Tseung et al. | 422/99 |
| 5,464,985 | A | 11/1995 | Cornish et al. | |
| 5,468,610 | A | 11/1995 | Polymeroulos et al. | |
| 5,498,545 | A | 3/1996 | Vestal | 436/47 |
| 5,503,980 | A | 4/1996 | Cantor | |
| 5,508,169 | A | 4/1996 | Deugau et al. | |
| 5,512,295 | A | 4/1996 | Kornberg et al. | 424/450 |
| 5,514,548 | A | 5/1996 | Krebber et al. | 435/6 |
| 5,532,227 | A | 7/1996 | Golub et al. | 514/152 |
| 5,538,897 | A | 7/1996 | Yates et al. | 436/89 |
| 5,547,835 | A | * 8/1996 | Koster | 435/6 |
| 5,580,434 | A | 12/1996 | Northup et al. | 422/102 |
| 5,580,733 | A | 12/1996 | Levis et al. | |
| 5,582,979 | A | 12/1996 | Weber | |
| 5,589,136 | A | 12/1996 | Northrup et al. | 422/102 |
| 5,599,500 | A | 2/1997 | Jones | 422/62 |
| 5,599,666 | A | 2/1997 | Schumm et al. | |
| 5,601,982 | A | 2/1997 | Sargent et al. | 435/6 |
| 5,605,662 | A | 2/1997 | Heller | 422/68.1 |
| 5,605,798 | A | 2/1997 | Koster | 435/6 |
| 5,607,912 | A | 3/1997 | Samejima et al. | 510/411 |
| 5,609,907 | A | 3/1997 | Natan | 427/2.12 |
| 5,622,824 | A | 4/1997 | Köster | |
| 5,625,184 | A | 4/1997 | Vestal et al. | |
| 5,627,369 | A | 5/1997 | Vestal et al. | |
| 5,643,800 | A | 7/1997 | Tarantino et al. | 436/518 |
| 5,650,489 | A | 7/1997 | Lam et al. | 530/334 |
| 5,654,150 | A | 8/1997 | King et al. | 435/6 |
| 5,663,242 | A | 9/1997 | Ghosh et al. | 525/329.4 |
| 5,670,322 | A | 9/1997 | Eggers et al. | 435/6 |
| 5,670,381 | A | 9/1997 | Jou et al. | 436/518 |
| 5,677,195 | A | 10/1997 | Winkler et al. | 436/518 |
| 5,688,642 | A | 11/1997 | Chrisey et al. | 435/6 |
| 5,691,141 | A | 11/1997 | Köster | |
| 5,700,642 | A | 12/1997 | Monforte et al. | |
| 5,710,028 | A | 1/1998 | Eyal et al. | 435/91.1 |
| 5,716,825 | A | 2/1998 | Hancock et al. | 435/286.5 |
| 5,743,960 | A | 4/1998 | Tisone | 118/683 |
| 5,756,050 | A | 5/1998 | Ershow et al. | 422/100 |
| 5,762,876 | A | 6/1998 | Lincoln et al. | 422/67 |
| 5,770,860 | A | 6/1998 | Franzen | 250/288 |
| 5,777,324 | A | 7/1998 | Hillenkamp | 250/288 |
| 5,789,395 | A | 8/1998 | Abramson et al. | 514/152 |
| 5,807,522 | A | 9/1998 | Brown et al. | 422/50 |
| 5,828,063 | A | 10/1998 | Koster et al. | 250/288 |
| 5,830,655 | A | * 11/1998 | Monforte et al. | 435/6 |
| 5,846,717 | A | 12/1998 | Brow et al. | 435/6 |
| 5,851,765 | A | 12/1998 | Köster | 435/6 |
| 5,869,240 | A | 2/1999 | Patterson | 435/6 |
| 5,869,242 | A | 2/1999 | Kamb | 435/6 |
| 5,872,003 | A | 2/1999 | Köster | 435/283.1 |
| 5,872,010 | A | 2/1999 | Karger et al. | 436/173 |
| 5,885,775 | A | 3/1999 | Haff et al. | 435/6 |
| 5,888,819 | A | 3/1999 | Goelet et al. | 435/5 |
| 5,900,481 | A | 5/1999 | Lough et al. | 536/55.3 |
| 5,925,520 | A | 7/1999 | Tully et al. | 435/6 |
| 5,927,547 | A | 7/1999 | Papen et al. | 222/57 |
| 5,928,906 | A | 7/1999 | Köster et al. | 435/91.2 |
| 5,965,363 | A | 10/1999 | Monforte et al. | 435/6 |
| 5,969,350 | A | 10/1999 | Kerley et al. | 250/287 |
| 5,976,798 | A | 11/1999 | Parker et al. | 435/6 |
| 5,985,356 | A | 11/1999 | Schultz et al. | 427/8 |
| 6,001,567 | A | 12/1999 | Brow et al. | 435/6 |
| 6,004,744 | A | 12/1999 | Goelett et al. | 435/5 |
| 6,006,171 | A | 12/1999 | Vines et al. | 702/184 |
| 6,022,688 | A | * 2/2000 | Jurinke et al. | 435/6 |
| 6,024,925 | A | 2/2000 | Little et al. | 422/100 |
| 6,040,193 | A | 3/2000 | Winkler et al. | 436/180 |
| 6,043,031 | A | 3/2000 | Köster et al. | 435/6 |
| 6,074,823 | A | 6/2000 | Köster | 435/6 |
| 6,110,426 | A | 8/2000 | Shalon et al. | 422/68.1 |
| 6,111,251 | A | 8/2000 | Hillenkamp | 250/288 |
| 6,121,048 | A | 9/2000 | Zaffaroni et al. | 436/45 |
| 6,133,436 | A | 10/2000 | Köster et al. | 536/24.3 |
| 6,136,269 | A | 10/2000 | Winkler et al. | 422/61 |
| 6,140,045 | A | 10/2000 | Wohlstadter et al. | 435/6 |
| 6,140,053 | A | 10/2000 | Köster | 435/6 |
| 6,146,854 | A | 11/2000 | Köster et al. | 435/1.1 |
| 6,194,144 | B1 | 2/2001 | Koster | 435/6 |
| 6,197,498 | B1 | 3/2001 | Koster | 435/5 |
| 6,207,370 | B1 | 3/2001 | Little et al. | 435/6 |
| 6,221,601 | B1 | 4/2001 | Köster et al. | 435/6 |
| 6,221,605 | B1 | 4/2001 | Köster | 435/6 |
| 6,225,061 | B1 | 5/2001 | Becker et al. | 435/6 |
| 6,225,450 | B1 | 5/2001 | Köster | 536/22.1 |
| 6,235,478 | B1 | 5/2001 | Köster | 435/6 |
| 6,238,871 | B1 | 5/2001 | Köster | 435/6 |
| 6,265,716 | B1 | 7/2001 | Hunter et al. | 250/288 |
| 6,268,131 | B1 | 7/2001 | Kang et al. | 435/6 |
| 6,277,573 | B1 | 8/2001 | Köster | 435/6 |
| 6,300,076 | B1 | 10/2001 | Köster | 435/6 |
| 6,303,309 | B1 | 10/2001 | Jurinke et al. | 435/6 |

OTHER PUBLICATIONS

Certified English translation of: Elov et al. "Synthesis of RNA using T7 RNA polymerase and immobilized DNA in a stream type reactor", *Bioorganicheskaia Khimia*, vol. 17 (6)789–94.

Chait et al., "Weighing naked proteins: pratical, high–accuracy mass measurement of peptides and proteins," *Science*, 257, 1885–1894 (1992).

Chee, "Enzymatic multiplex DNA sequencing," *Nucleic Acids Res.* 19(12):3301–3305 (1991).

Collins et al., "A DNA Polymorphism Discovery Resource for Research on Human Genetic Variation", *Genome Res.*, 8:1229–1231, (1998).

Derwent #009135586, WPI Acc No. 1992–263024, for Japanese Patent JP 4178359, "New antiinflamatory tretracycline derivs.—for treating articular rheumatism, osteoarthritis, Reiter's syndrome, Lyme disease, etc.".

Derwent #010643408, WPI Acc No. 1996–140362, for German Patent DE 4431174 A, "Detecting tumour specific mRNA by conversion to cDNa and amplification –provides early, sensitive and specific diagnosis and monitoring, partic. by analysis of blood or sputum".

Derwent #010725941, WPI Acc No. 1996–222896, for German Patent DE 4438630 A, "Amplification of non–characterized DNA fragments –using only a single primer, with formation of hairpin loops during second strand synthesis".

Elov et al. "Synthesis of RNA using T7 RNA polymerase and immobilized DNA in a stream type reactor", *Bioorganicheskaia Khimia, vol.* 17(6)789–94.

English version of Japanese Patent, JP2215399 A 90028 DW9040, WPI/Derwent, AN90–302767, Method detect DNA de single strand combination DNA prime correspond base sequence forming replica.

English version of Japanese Patent, JP63230086 A 880926 DW8844, WPI/Derwent, AN88–311964, Carry immobilise physiological active substance comprise bind chain form di sulphide compound epoxy group latex contain polymer particle.

Feng et al., "The RNA Component of Human Telomerase", *Science* 269(5228):1236–1241 (1995).

Foster, M.W. and Freeman, W.L., "Naming Names in Human Genetic Variation Research", *Genome Res.*, 8:755–757, (1998).

George et al. "Current Methods in Sequence Comparison and Analysis," Chapter 12 of: Macromolecule Sequencing and Synthesis, Selected Methods and Applications Schlesinger (Ed.), 127–149, (1988).

Ji et al., Two–dimensional electrophoretic analysis of proteins expressed by normal and cancerous human crypts: application of mass spectrometry to peptide–mass fingerprinting, *Electrophoresis* 15: 391–405 (1994).

Khapro et al. "A method for DNA seqencing by hybridization with oligonucleotide matrix" J. DNA Sequencing and Mapping v1;375–388, (1991).

Lagerstrom et al. "PCR Methods and applications" 1:111–119 (1991).

Liu et al., "Use of a Nitrocellulose Film Substrate in Matrix–Assisted Laser Desorption/Ionization Mass Spectrometry for DNA Mapping and Screening", *Anal. Chem.* 67:3482–3490 (1995).

Naito et al., "Detection of Tyrosine Hydroxylase mRNA and Minimal Neuroblastoma Cells by the Reverse Transcription– Polymerase Chain Reaction", *European Journal of Cancer* 27:762–765 (1991).

O'Donnell–Maloney et al., "The development of microfabricated arrays for DNA sequencing and analysis" *TIBTECH* 14:401–407 (1996).

Olsson, "Isolation and Characterization of a tumor necrosis factor binding protein from urine," *Eur. J. Haematol.,* 42:270–275 (1989) (XP000937599).

Ordoukhanian et al., "Design and synthesis of a Versatile Photocleavable DNA building Block. Application to Phototriggered Hybridization," *J. Am. Chem. Soc.* 117:9570–9571 (1995).

Palejwala et al., "Quantitative multiplex sequence analysis of mutational hot spots. Frequency and specificity of mutations induced by a site–specific ethenocytosine in m13 viral DNA," *Biochemistry* 32:4105–4111 (1993).

Pasini et al., "RET mutations in human disease," *Trends in Genetics* 12(4):138–144 (1996).

Sarkar et al., "Human Genetic Bi–allelic Sequences (HGBASE), a Database of Intra–genic Polymorphisms", 93(5):693–694, (1998).

Seckinger et al., "Purification and Biologic Characterization of a Specific Tumor Necrosis Factor Alpha Inhibitor", *J. Biochem.*, 264/20:11966–11973 (1989) (XP000673302 ISSN: 0021–9258 cited in the application).

Siuzdak et al., "The emergence of mass spectrometry in biochemical research," *PNAS* 91, 11290–11297 (1994).

Syvanen et al., "Detection of Point Mutations by Solid–Phase Methods," *Human Mutation* 3(3):172–179 (1994).

Zuckermann et al., "Efficient methods for attachment of thiol specific probes to the3'–ends of synthetic oligodeoxyribonucleotides," *Nucleic Acids Research*, 15:13, 5305–5321 (1987).

Abrams, et al,. "Comprehensive Detection of Single Base Changes in Human Genomic DNA Using Denaturing Gradient Gel Electrophoresis and a GC Clamp," *Genomics*, 7:463–475, 1990.

Lee, et al., "DNA Sequencing with Dye–Labeled Terminators and T7 DNA Polymerase: Effect of Dyes and DNTPs on Incorporation of Dye–Terminators and Probability Analysis of Termination Fragments," *Nucleic Acids Research*, 20(10):2471–2483, 1992.

Mag, et al., "Synthesis and Selective Cleavage of an Oligodeoxynucleotide Containing a Bridged Internucleotide 5'–Phosphorothioate Linkage," *Nucleic Acids Research*, 19(7):1437–1441, 1991.

Orita, et al., "Detection of Polymorphisms of Human DNA by Gel Electrophoresis as Single–Strand Conformation Polymorphisms," *Proc. Natl. Acad. Sci. USA*, 86:2766–2770, 1989.

Pease, et al., "Light–Generated Oligonucleotide Arrays for Rapid DNA Sequence Analysis," *Proc. Natl. Acad. Sci. USA*, 91:5022–5026, 1994.

Richterich, et al., "Cytosine Specific DNA Sequencing with Hydrogen Peroxide," *Nucleic Acids Research*, 23(23):4922–4923, 1995.

Saleeba, et al., "Chemical Cleavage of Mismatch to Detect Mutations," *Method Enzymology*, 217:286–295, 1993.

Sandaltzopoulos and Becker "Solid–Phase DNase I Footprinting," *Biochemica*, 4:25–27, 1995.

Shaler, et al., "Effect of Impurities on the Matrix–Assisted Laser Desorption Mass Spectra of Single–Stranded Oligodeoxynucleotides," *Anal. Chem.,* 68(3):576–579, 1996.

Spengler, et al., "Laser Mass Analysis in Biology," *Ber. Bunsenqes Phys. Chem.,* 93(3):396–402, 1989.

Szbalski, "Universal Restriction Endonuclease: Designing Novel Cleavage Specificities by Combining Adapter Oligodeoxynucleotide and Enzyme Moieties," *Gene*, 40:169–173, 1985.

Tanaka, et al., "Protein and Polymer Analyses up to m/z 100 000 by Laser Ionization Time–of–flight Mass Spectrometry," *Rapid Commun. in Mass Spectrometry*, 2:151–153, 1988.

Tang, et al., "Matrix–Assisted Laser Desorption/Ionization of Restriction Enzyme–Digested DNA," *Rapid Commun. in Mass Spectrometry*, 8:183–186, 1994.

Uhlmann and Peyman "Antisense Oligonucletides: A New Therapeutic Principle," *Chemical Reviews*, 90(4):543–584, 1990.

Wang, et al., "DNA Sequencing from Single Phage Plaques Using Solid–Phase Magnetic Capture," *BioTechniques*, 18(1):130–135, 1995.

Wu, et al., "Matrix–Assisted Laser Desorption Time–of–Flight Mass Spectrometry of Oligonucleotides Using 3–Hydroxypicolinic Acid as an Ultraviolet–sensitive Matrix," *Rapid Commun. in Mass Spectrometry*, 7:142–146, 1993.

Youil, et al., "Screening for Mutations by Enzyme Mismatch Cleavage with T4 Endonuclease VII," *Proc. Natl. Acad. Sci. USA*, 92:87–91, 1995.

Bergh, et al., "Complete Sequencing of the p53 Gene Provides Prognostic Information in Breast Cancer Patients, Particularly in Relation to Adjuvant Systemic Therapy and Radiotherapy," *Nature Medicine*, 1:1029–1034, 1995.

Fang, et al., "Simultaneous Analysis of Mutant and Normal Alleles for Multiple Cystic Fibrosis Mutations by the Ligase Chain Reaction," *Human Mutaion*, 6:144–151, 1995.

Bai, Jian, et al., "Procedures for Detection of DNA by Matrix–Assisted Laser Desorption/Ionization Mass Spectrometry Using a Modified Nafion Film Substrate," *Rapid Commun. in Mass Spectrometry*, 9:1172–1176, 1995.

Bai, Jian, et al., "Matrix–Assisted Laser Desorption/Ionization Mass Spectrometry of Restriction Enzyme–Digested Plasmid DNA Using an Active Nafion Substrate," *Rapid Commun. in Mass Spectrometry*, 8:687–691, 1994.

Benner and Jaklevic, "DNA Base–Pair Substitutions Detected in Double–Stranded DNA With Matrix–Assisted Laser Desorption/Ionization Time–of–Flight Mass Spectrometry," *Eur. Mass Spectrum.*, 479–485, 1995.

Chang, et al., "Detection of ΔF508 Mutation of the Cystic Fibrosis Gene by Matrix–Assisted Laser Desorption/Ionization Mass Spectrometry," *Rapid Commun. in Mass Spectometry*, 9:772–774, 1995.

Fenn, et al., "Electrospray Ionization for Mass Spectrometry Large Biomolecules," *Science*, 246:64–71, 1989.

Jurinke, Christian, et al., "Analysis of Ligase Chain Reaction Products Via Matrix–Assisted Laser Desorption/Ionization Time–of–Flight–Mass Spectrometry," *Analytical Biochemistry*, 237:174–181, 1996.

Kuimelis and McLaughlin," Cleavage Properties of an Oligonucleotide Containing a Bridged Internucleotide 5'-phosphorothioate RNA Linkage," *Nucleic Acids Research*, 23:4753–4760, 1995.

Lee, et al., Comparison on Short Tandem Repeat (STR) Detection Using Silver, Fluorescence and Matrix Assisted Laser Desorption Ionization Time–of–Flight Mass Spectrophotometry (MALDITOF–MS), *Proceedings of the Sixth International Symposium on Human Identification*, published by Promega Corp., 1995.

Liang, Gangning, et al., "The Use of 2–Hydroperoxytetrahydrofuran as a Reagent to Sequence Cytosine and to Probe Non–Watson–Crick DNA Structures," *Nucleic Acids Research*, 23(4):713–719, 1995.

Liu, Yan–Hui, et al., "Use of a Nitrocellulose Film Substrate in Matrix–Assisted Laser Desorption/Ionization Mass Spectrometry for DNA Mapping and Screening," *Anal. Chem.*, 67:3482–3490, 1995.

Liu, Yan–Hui, et al., "Rapid Screening of Genetic Polymorphisms Using Buccal Cell DNA with Detection by Matrix–Assisted Laser Desorption/Ionization Mass Spectrometry," *Rapid Commun. in Mass Spectrometry*, 9:735–743, 1995.

Tang, et al., "Laser Mass Spectrometry of Polydeoxyribothymidylic Acid Mixtures," *Rapid Commun. Mass Spectrom*, 7:63–66, 1993.

Benner, Horn, Katz, Jaklevic, "Identification of Denatured Double–stranded DNA by Matrix–Assisted Laser Desorption/Ionization Time–of–Flight Mass Spectrometry," *Rapid Commun. in Mass Spectrom.*, 9:537–540, 1995.

Hegner, Wagner, Semenza, "Ultralarge Atomically Flat Template–Stripped Au Surfaces for Scanning Probe Microscopy," *Surface Science*, 291:39–46, 1993.

Kirpekar, Nordhoff, Kristiansen, Roepstorff, Lezius, Hahner, Karas, Hillenkamp, "Matrix Assisted Laser Desorption/Ionization Mass Spectrometry of Enzymatically Synthesized RNA Up to 150 kDA," *Nucleic Acids Research*, 22(19):3866–3870, 1994.

Nelson, Dogruel, Williams, "Detection of Human IgM at M/z~1 Mda," *Rapid Commun. in Mass Spectrom.*, 9:7, 1995.

Newman, Nwosu, Williams, Cosstick, Seela, Connolly, "Incorporation of a Complete Set of Deoxyadenosine and Thymidine Analogues Suitable for the Study of Protein Nucleic Acid Interactions into Oligodoexynucleotides," *Biochemistry*, 29:9891–9901, 1990.

Shaw, Madison, Sood, Spielvogel, "Oligonucleoside Boranophosphate (Boran Phosphonate)," *In: Methods in Molecular Biology, vol. 20: Protocols for Oligonucleotides and Analogs*, S. Agrawal (Ed.), Humana Press Inc., Totowa, NJ, Chapter 11, 224:243, 1993.

Soukup, Cerny, Maher III, "Preparation of Oligonucleotide—Biotin Conjugates with Cleavable Linkers," *Bioconjugate Chem.*, 6:135–138, 1995.

Wu, Shaler, Becker, "Time–of Flight Mass Spectrometry of Underivatized Single–Stranded DNA Oligomers by Matrix–Assisted Laser Desorption," *Anal. Chem.*, 66:1637–1645, 1994.

International Search Report dated Jan. 20, 1998(PCT/US 97/17101) (GETR:018P).

Sedlak, "GeneTrace Systems Bets its Future in Genomics on TOF Mass Spectroscopy," *Genetic Engineering News*, 16(21):, 1996. (website: http://www.genetrace.com).

Tang et al., "Detection of 500–Nucleotide DNA by Laser Desorption Mass Spectrometry," *Rapid Commun. in Mass Spectrometry*, 8(9):727–730, 1994.

Arnott et al., "Construction and performance of a laser desorption/ionization TOF mass spectrometer system: applications to problems in peptide, protein, and DNA structural analysis," *The 40th ASMS Conference on Mass Spectrometry and Allied Topics*, May 31–Jun. 5, Washington, D.C., pp. 328–329, 1992.

Bevan et al., "The analysis of oligonucleotides and their phosphoramidate analogues by LSIMS mass spectrometry," *The 39th ASMS Conference on Mass Spectrometry and Allied Topics*, pp. 983–984, 1989.

Edmonds et al., "Electrospray ionization mass spectrometry and tandem mass spectrometry of small oligonucleotides," *37th ASMS Conference on Mass Spectrometry and Allied Topics*, May 21–26, Miami Beach, FL, pp. 844–845, 1989.

Jacobson et al., "Applications of mass spectrometry to DNA sequencing,", *GATA*, 8(8):223–229, 1991.

Karas and Bahr, "Matrix–assisted laser desorption ionization mass spectrometry," *Mass Spectrometry Reviews,* 10:335–357, 1991.

Limbach et al., "Characterization of oligonucleotides and nucleic acids by mass spectrometry," *Current Opinion Biotechnology,* 6:96–102, 1995.

McNeal et al., "A new method for the analysis of fully protected oligonucleotides by $^{252}$ Cf–plasma desorption mass spectrometry. 3. Positive ions," *J. Am. Chem. Soc.,* 104:981–984, 1982.

Mizusawa et al., "Improvement of the dideoxy chain termination method of DNA sequencing by use of deoxy–7–deazaguanosine triphosphate in place of dGTP," *Nucl. Acids Res.,* 14(3):1319–1325, 1986.

Mock et al., "Sample immobilization protocols for matrix assisted laser desorption mass spectrometry," *The 40th ASMS Conference on Mass Spectrometry and Allied Topics,* pp. 1921–1922, 1992.

Musser and Kelley, "Sensitivity enhancement for static and continuous flow FAB/MS analysis of nucleotides by quaternary amine surfactants," *The 39th ASMS Conference on Mass Spectrometry and Allied Topics,* pp. 374–375, 1989.

Nordhoff et al., "Matrix–assisted laser desorption/ionization mass spectrometry of nucleic acids with wavelengths in the ultraviolet and infrared," *Rapid Comm. Mass Spectrometry,* 6:771–776, 1992.

Overberg et al., "Laser desorption mass spectrometry, Part II performance and applications of matrix–assisted laser desorption/ionization of large biomolecules," *Anal. Chem.,* 181–197, 1992.

Parr et al., "Matrix–assisted laser desorption/ionization mass spectrometry of synthetic oligodeoxyribonucleotides," *Rapid Comm. Mass Spectrometry,* 6:369–372, 1992.

Spengler et al., "Molecular weight determination of underivatized oligodeoxyribonucleotides by positive–ion matrix–assisted ultraviolet laser–desorption mass spectrometry," *Rapid Comm. Mass Spectrometry,* 4(4):99–102, 1990.

Stahl et al., "Solid phase DNA sequencing using the biotin–avidin system," *Nucl. Acids Res.,* 16(7):3025–3039, 1988.

Stults and Marsters, "Characterization of oligodeoxynucleotide conjugates by electrospray ionization mass spectrometry," *Proceedings of the 39th ASMS Conference on Mass Spectrometry and Allied Topics,* May 19–24, Nashville, TN, pp. 1161–1162, 1991.

Stults and Marsters, "Improved electrospray ionization of synthetic oligodeoxynucleotides," *Rapid Comm. Mass Spectrometry,* 5:359–363, 1991.

Tong and Smith, "Solid–phase method for the purification of DNA sequencing reactions," *Anal. Chem.,* 64:2672–2677, 1992.

Trainor, "DNA sequencing, automation, and the human genome," *Anal. Chem.,* 62:418–426, 1990.

Cosstick et al., "Synthesis and properties of dithymidine phosphate analogues containing 3'–thiothymidine" Nucleic Acids Research vol. 18, pp. 829–835, 1990.*

* cited by examiner

Positive ion TOF mass spectra obtained from 200 fmoles of DNA in 3-HPA. Each spectrum is a sum of 100 laser pulses at 266 nm. (a) a single-stranded 72-mer which also shows a 71-mer. The FWHM resolution is 240. Clearly resolving matrix adducts (labelled M).
(b) 88-mer parent peak has a resolution of 330.

Mass Spectra of a heterozygous mix of wild type and mutant where A has mutated to T. Spectral peaks are separated by 9 mass units.

Mass Spectra of a heterozygous mix of wild type and mutant where A has mutated to T. T has been replaced by heptynydeoxyuridine during amplification of the mutant region. Spectral peaks are now separated by 65 mass units.

METHODS OF PREPARING NUCLEIC ACIDS FOR MASS SPECTROMETRIC ANALYSIS

CROSS-REFERENCE TO RELATED APPLICATIONS

This application is a divisional of application Ser. No. 08/759,993, filed Dec. 2, 1996 now U.S. Pat. No. 5,965,363 and a continuation-in-part of U.S. application Ser. No. 08/715,582, filed Sep. 19, 1996.

ACKNOWLEDGEMENTS

This invention was supported in part by a Financial Assistance Award from the United States Department of Commerce, Advanced Technology Program, Cooperative Agreement #70NANB5H1029. The U.S. Government may have rights in this invention.

INTRODUCTION

Approximately 4,000 human disorders are attributed to genetic causes. Hundreds of genes responsible for various disorders have been mapped, and sequence information is being accumulated rapidly. A principal goal of the Human Genome Project is to find all genes associated with each disorder. The definitive diagnostic test for any specific genetic disease (or predisposition to disease) will be the identification of polymorphic variations in DNA sequence in affected cells that result in alterations of gene function. Furthermore, response to specific medications may depend on the presence of polymorphisms. Developing DNA (or RNA) screening as a practical tool for medical diagnostics requires a method that is inexpensive, accurate, expeditious, and robust.

Genetic polymorphisms and mutations can manifest themselves in several forms, such as point polymorphisms or point mutations where a single base is changed to one of the three other bases, deletions where one or more bases are removed from a nucleic acid sequence and the bases flanking the deleted sequence are directly linked to each other, insertions where new bases are inserted at a particular point in a nucleic acid sequence adding additional length to the overall sequence, and expansions and reductions of repeating sequence motifs. Large insertions and deletions, often the result of chromosomal recombination and rearrangement events, can lead to partial or complete loss of a gene. Of these forms of polymorphism, in general the most difficult type of change to screen for and detect is the point polymorphism because it represents the smallest degree of molecular change. Wild type is a standard or reference nucleotide sequence to which variations are compared. As defined, any variation from wild type is considered a polymorphism including naturally occurring sequence variations and pathogenic mutations.

Although a number of genetic defects can be linked to a specific single point mutation within a gene, e.g. sickle cell anemia, many are caused by a wide spectrum of different mutations throughout the gene. A typical gene that might be screened using the methods described here could be anywhere from 1,000 to 100,000 bases in length, though smaller and larger genes do exist. Of that amount of DNA, only a fraction of the base pairs actually encode the protein. These discontinuous protein coding regions are called exons and the remainder of the gene is referred to as introns. Of these two types of regions, exons often contain the most important sequences to be screened. Several complex procedures have been developed for scanning genes in order to detect polymorphisms, which are applicable to both exons and introns.

In terms of current use, most of the methods to scan or screen genes employ slab or capillary gel electrophoresis for the separation and detection step in the assays. Gel electrophoresis of nucleic acids primarily provides relative size information based on mobility through the gel matrix. If calibration standards are employed, gel electrophoresis can be used to measure absolute and relative molecular weights of large biomolecules with some moderate degree of accuracy; even then typically the accuracy is only 5% to 10%. Also the molecular weight resolution is limited. In cases where two DNA fragments with identical number of base pairs can be separated, using high concentration polyacrylamide gels, it is still not possible to identify which band on a gel corresponds to which DNA fragment without performing secondary labeling experiments. Gel electrophoresis techniques can only determine size and cannot provide any information about changes in base composition or sequence without performing more complex sequencing reactions. Gel-based techniques, for the most part, are dependent on labeling or staining methods to visualize and discriminate between different nucleic acid fragments.

All of the methods in use today capable of screening broadly for genetic polymorphisms suffer from technical complication and are labor and time intensive. Single strand conformational polymorphism (SSCP) (Orita et al., "Detection of Polymorphisms of Human DNA by Gel Electrophoresis as Single-Stranded Conformation Polymorphisms," Proc. Natl. Acad. Sci. USA 86, 2766 (1989)), denaturing gradient gel electrophoresis (DGGE) (Abrams et al., "Comprehensive Detection of Single Base Changes in Human Genomic DNA Using Denaturing Gradient Gel Electrophoresis and a GC Clamp," Genomics 7, 463 (1990)), chemical cleavage at mismatch (CCM) (J. A. Saleeba & R. G. H. Cotton, "Chemical Cleavage of Mismatch to Detect Mutations," Methods in Enzymology 217, 286 (1993)), enzymatic mismatch cleavage (EMC) (R. Youil et al., "Screening for Mutations by Enzyme Mismatch Cleavage with T4 Endonuclease VII," Proc. Natl. Acad. Sci. USA 92, 87 (1995)), and "cleavase" fragment length polymorphism (CFLP) procedures are currently gel-based, making them cumbersome to automate and perform efficiently. There is a need for new methods that can provide cost effective and expeditious means for screening genetic material in an effort to reduce medical expenses. The inventions described here address these issues by developing novel, tailor-made processes that focus on the use of mass spectrometry as a genetic analysis tool. Mass spectrometry requires minute samples, provides extremely detailed information about the molecules being analyzed including high mass accuracy, and is easily automated.

The late 1980's saw the rise of two new mass spectrometric techniques for successfully measuring the masses of intact very large biomolecules, namely, matrix-assisted laser desorption/ionization (MALDI) time-of-flight mass spectrometry (TOF MS) (K. Tanaka et al., "Protein and Polymer Analyses up to m/z 100,000 by Laser Ionization Time-of-flight Mass Spectrometry," Rapid Commun. Mass Spectrom. 2, 151–153 (1988); B. Spengler et al., "Laser Mass Analysis in Biology," Ber. Bunsenges. Phys. Chem. 93, 396–402 (1989)) and electrospray ionization (ESI) combined with a variety of mass analyzers (J. B. Fenn et al., Science 246, 64–71 (1989)). Both of these two methods are suitable for genetic screening tests. The MALDI mass spectrometric technique can also be used with methods other than time-of-flight, for example, magnetic sector, Fourier-transform ion cyclotron resonance, quadrupole, and quadrupole trap. One of the advances in MALDI analysis of polynucleotides was the discovery of 3-hydroxypicolinic acid as a matrix for mixed-base oligonucleotides. Wu, et al., Rapid Comm'ns in Mass Spectrometry, 7:142–146 (1993).

MALDI-TOF MS involves laser pulses focused on a small sample plate comprising analyte molecules (nucleic acids) embedded in either a solid or liquid matrix comprising a small, highly absorbing compound. The laser pulses transfer energy to the matrix causing a microscopic ablation and concomitant ionization of the analyte molecules, producing a gaseous plume of intact, charged nucleic acids in single-stranded form. If double-stranded nucleic acids are analyzed, the MALDI-TOF MS typically results in mostly denatured single-strand detection. The ions generated by the laser pulses are accelerated to a fixed kinetic energy by a strong electric field and then pass through an electric field-free region in vacuum in which the ions travel with a velocity corresponding to their respective mass-to-charge ratios (m/z). The smaller m/z ions will travel through the vacuum region faster than the larger m/z ions thereby causing a separation. At the end of the electric field-free region, the ions collide with a detector that generates a signal as each set of ions of a particular mass-to-charge ratio strikes the detector. Usually for a given assay, 10 to 100 mass spectra resulting from individual laser pulses are summed together to make a single composite mass spectrum with an improved signal-to-noise ratio.

The mass of an ion (such as a charged nucleic acid) is measured by using its velocity to determine the mass-to-charge ratio by time-of-flight analysis. In other words, the mass of the molecule directly correlates with the time it takes to travel from the sample plate to the detector. The entire process takes only microseconds. In an automated apparatus, tens to hundreds of samples can be analyzed per minute. In addition to speed, MALDI-TOF MS has one of the largest mass ranges for mass spectrometric devices. The current mass range for MALDI-TOF MS is from 1 to 1,000,000 Daltons (Da) (measured recently for a protein). R. W. Nelson et al., "Detection of Human IgM at m/z~1 MDa," Rapid Commun. Mass Spectrom. 9, 625 (1995).

The performance of a mass spectrometer is measured by its sensitivity, mass resolution and mass accuracy. Sensitivity is measured by the amount of material needed; it is generally desirable and possible with mass spectrometry to work with sample amounts in the femtomole and low picomole range. Mass resolution, $m/\Delta m$, is the measure of an instrument's ability to produce separate signals from ions of similar mass. Mass resolution is defined as the mass, m, of a ion signal divided by the full width of the signal, $\Delta m$, usually measured between points of half-maximum intensity. Mass accuracy is the measure of error in designating a mass to an ion signal. The mass accuracy is defined as the ratio of the mass assignment error divided by the mass of the ion and can be represented as a percentage.

To be able to detect any point polymorphism directly by MALDI-TOF mass spectrometry, one would need to resolve and accurately measure the masses of nucleic acids in which a single base change has occurred (in comparison to the wild type nucleic acid). A single base change can be a mass difference of as little as 9 Da. This value represents the difference between the two bases with the closest mass values, A and T (A=2'-deoxyadenosine-5'-phosphate=313.19 Da; T=2'-deoxythymidine-5'-phosphate=304.20 Da; G=2'-deoxyguanosine-5'-phosphate=329.21 Da; and C=2'-deoxycytidine-5'-phosphate=289.19 Da). If during the mutation process, a single A changes to T or a single T to A, the mutant nucleic acid containing the base transversion will either decrease or increase by 9 in total mass as compared to the wild type nucleic acid. For mass spectrometry to directly detect these transversions, it must therefore be able to detect a minimum mass change, $\Delta m$, of approximately 9 Da.

For example, in order to fully resolve (which may not be necessary) a point-mutated (A to T or T to A) heterozygote 50-base single-stranded DNA fragment having a mass, m, of ~15,000 Da from its corresponding wild type nucleic acid, the required mass resolution is $m/\Delta m=15,000/9 \approx 1,700$. However, the mass accuracy needs to be significantly better than 9 Da to increase quality assurance and to prevent ambiguities where the measured mass value is near the half-way point between the two theoretical masses. For an analyte of 15,000 Da, in practice the mass accuracy needs to be $\Delta m \sim \pm 3$ Da=6 Da. In this case, the absolute mass accuracy required is $(6/15,000)*100=0.04\%$. Often a distinguishing level of mass accuracy relative to another known peak in the spectrum is sufficient to resolve ambiguities. For example, if there is a known mass peak 1000 Da from the mass peak in question, the relative position of the unknown to the known peak may be known with greater accuracy than that provided by an absolute, previous calibration of the mass spectrometer.

In order for mass spectrometry to be a useful tool for screening for polymorphisms in nucleic acids, several basic requirements need to be met. First, any nucleic acids to be analyzed must be purified to the extent that minimizes salt ions and other molecular contaminants that reduce the intensity and quality of the mass spectrometric signal to a point where either the signal is undetectable or unreliable, or the mass accuracy and/or resolution is below the value necessary to detect the type of polymorphism expected. Second, the size of the nucleic acids to be analyzed must be within the range of the mass spectrometry-where there is the necessary mass resolution and accuracy. Mass accuracy and resolution do significantly degrade as the mass of the analyte increases; currently this is especially significant above approximately 30,000 Da for oligonucleotides (~100 bases), impacting the detection of single nucleotide polymorphisms (SNPs) above said mass value. Third, because all molecules within a sample are visualized during mass spectrometric analysis (i.e. it is not possible to selectively label and visualize certain molecules and not others as one can with gel electrophoresis methods) it is necessary to partition nucleic acid samples prior to analysis in order to remove unwanted nucleic acid products from the spectrum. Fourth, the mass spectrometric methods for generalized nucleic acid screening must be efficient and cost effective in order to screen a large number of nucleic acid bases in as few steps as possible.

The methods for detecting nucleic acid polymorphisms known in the art do not satisfy these four requirements. For example, prior art methods for mass spectrometric analysis of DNA fragments have focussed on double-stranded DNA fragments which result in complicated mass spectra, making it difficult to resolve mass differences between two complementary strands. See, e.g., Tang et al., Rapid Comm'n. in Mass Spectrometry, 8:183–186 (1994). Moreover, the prior art has not provided optimal methods for isolating single-stranded amplified target nucleic acids to improve mass accuracy in higher mass ranges.

Thus, there is a need for cost and time effective methods of detecting genetic polymorphisms using mass spectrometry, preferably MALDI or ESI, and with mass accuracy of a few parts in 10,000 or better.

SUMMARY OF THE INVENTION

The present invention comprises several aspects, including (1) procedures for reducing the length of target nucleic acids to remove one or more flanking polynucleotide regions that flank the regions of interest, which contain or are suspected to contain a polymorphism; (2) procedures for isolating either single-stranded or double-stranded target nucleic acids for mass spectrometric analysis; and (3) procedures combining these two aspects; and (3) kits for the methods described herein.

The methods for reducing the length of target nucleic acids, preferably in amplified form, eliminate unnecessary sequences and by reducing the length also reduce the mass of the resulting single-stranded or double-stranded target nucleic acids, which increases mass resolution and accuracy. The target nucleic acids may be reduced in length by any of the methods known that will cleave within one or more flanking regions preferably without cleaving within the region of interest. Exemplary methods of reducing length include: cleaving at endogenous restriction endonuclease cleavable sites present in one or more flanking regions but absent in the region of interest; cleaving at restriction endonuclease cleavable sites at or adjacent to restriction endonuclease recognition sites incorporated into one or more flanking regions by use of one or more cleavable primers comprising said restriction endonuclease recognition sites; cleaving at a combination of restriction endonuclease cleavable sites wherein the sites are endogenous and/or introduced using mismatch or overhanging primers; and selective digestion of one or more flanking regions using exonuclease. The restriction endonucleases can include type II and type IIS restriction endonucleases. The restriction endonuclease recognition sites can be either within a primer region, or outside the primer region, so long as the restriction endonuclease cleavable sites are within one or more flanking regions and preferably not within a region of interest. For type II restriction endonucleases, the restriction endonuclease recognition site is the same as the restriction endonuclease cleavable site. For Type IIS restriction endonucleases, the cleavable site is at a defined distance away from one side of the recognition site. Accordingly, cleavable primers may contain one or more restriction recognition sites of one or more different restriction endonucleases, one or more cleavable sites of one or more different restriction endonucleases, one or more exonuclease blocking moieties, or a combination thereof.

Another embodiment of the invention involves reducing the length of an amplified target nucleic acid and isolating a single-stranded amplified target nucleic acid at the same time by using a cleavable primer having an exonuclease blocking moiety. After amplification of the target nucleic acid, the amplified target nucleic acid comprises an exonuclease blocking moiety. The amplified target nucleic acid is then treated with a 5' to 3' exonuclease, which degrades the strand containing the exonuclease blocking moiety in a 5' to 3' direction only up to the blocking moiety. The 5' to 3' exonuclease can optionally completely degrade the other strand of the amplified target nucleic acid, in cases wherein the other strand does not have an exonuclease blocking moiety. The treatment with the 5' to 3' exonuclease leaves a reduced-length, single-stranded amplified target nucleic acid for mass spectrometric analysis.

Yet another embodiment of the invention involves use of cleavable primers to reduce the length of an amplified target nucleic acid. An amplified target nucleic acid can be reduced in length by cleaving off at least a portion of one or more flanking regions comprising a cleavable site, wherein the cleavable site is introduced via a cleavable primer, wherein the cleavable site is located outside of the region of interest. Cleavable primers of the invention include those comprising an exonuclease blocking moiety, a Type IIS restriction endonuclease recognition site, and a Type II restriction endonuclease recognition site, but does not include a Type II restriction endonuclease recognition site where one of the complementary strands cannot be cleaved by a Type II restriction endonuclease.

The present invention also provides methods for isolating single-stranded or double-stranded amplified target nucleic acids. At least one strand of an amplified target nucleic acid can be bound to a solid support to permit rigorous washing to remove salt adducts, unwanted oligonucleotides and enzymes. Either a double-stranded amplified target nucleic acid or a single-stranded amplified target nucleic acid, whether the bound strand or the unbound strand, can be isolated for mass spectrometric analysis. Cleavable linkers or cleavable primers can be used to release the bound strands from the solid support. The isolation provides significantly improved mass resolution and accuracy in large mass ranges. Also, the isolation of either single-stranded or double-stranded amplified target nucleic acids occurs prior to the application of the nucleic acids to the matrix solution, which results in well-defined mass spectral peaks and enhanced mass accuracy. The matrix solution can be any of the known matrix solutions used for mass spectrometric analysis, including 3-hydroxypicolinic acid, nicotinic acid, picolinic acid, 2,5-dihydroxybenzoic acid, nitrophenol.

The present invention provides methods of detecting polymorphisms in one or more target nucleic acids comprising: amplifying at least one target nucleic acid, wherein said amplified target nucleic acid comprises a region of interest and optionally one or more flanking regions; reducing the length of at least one of said amplified target nucleic acids comprising cleaving off a portion of one or more flanking regions, and determining the masses of each of said reduced-length amplified target nucleic acids using a mass spectrometer. This method can be used to detect polymorphisms in a single target nucleic acid by detecting variability in mass as compared to a wild type target nucleic acid or other "alleles" of said target nucleic acid.

In another embodiment, methods are provided for detecting polymorphisms in at least one target nucleic acid comprising: amplifying at least one target nucleic acid, wherein said amplified target nucleic acid comprises a region of interest and optionally one or more flanking regions, isolating either a positive or negative strand of said amplified target nucleic acid to form a single-stranded amplified target nucleic acid and determining the masses of each single-stranded amplified target nucleic acid using a mass spectrometer.

In yet another embodiment, methods are provided for detecting polymorphisms in at least one target nucleic acid comprising: amplifying at least one target nucleic acid, wherein said amplified target nucleic acid comprises a region of interest and optionally one or more flanking regions, reducing the length of at least one of said amplified target nucleic acids comprising cleaving off a portion of one or more flanking regions, isolating either a positive or negative strand of said amplified target nucleic acid to form an amplified target nucleic acid, and determining the mass of each single-stranded amplified target nucleic acid using a mass spectrometer.

In the amplification methods, it is preferred that at least one of the primers be designed to be close to the polynucleotide region of interest, generally within 40 nucleotides.

The methods can also be used to detect polymorphisms in a set of different target nucleic acids, comprising amplifying each of said target nucleic acids, reducing length and/or isolating a single-strand of each of said amplified target nucleic acids, and determining the mass of each of said single-strands of said amplified target nucleic acids using mass spectrometry. Thus, these methods can be used to detect polymorphisms in a plurality of different target nucleic acids simultaneously.

The target nucleic acids can comprise any polynucleotide sequence that contains or is suspected of containing a polymorphism, including but not limited to short tandem repeats (STRs), simple sequence length polymorphisms (SSLP), single nucleotide polymorphisms (SNPs), and the multitude of disease markers, for example, markers for sickle cell anemia, fragile X disorder, cystic fibrosis, Tay Sachs disease, Gaucher disease, thalassemias, and cancer-related genes. The preferably single-stranded amplified target nucleic acids can be any size that can be adequately resolved by mass spectrometric analysis. Preferably, in cases where a SNP is to be detected, the final product single-stranded amplified target nucleic acids are less than 100 bases in length. Most preferably, the final product, single-stranded amplified target nucleic acids are from 10 to 90 bases in length. The nature of the mutation to be detected is a factor in the size limitations for optimum mass resolution. For example, as described above for SNPs, the maximum size limit is approximately 100 nucleotides in length. For microsatellite repeats and other two nucleotide repeats, the maximum size limit is approximately 200 nucleotides in length. For four-nucleotide repeats, the maximum size limit is approximately 300 nucleotides. One of ordinary skill in the art will appreciate that as mass spectrometric techniques for analysis of nucleic acids improve, the sizes of single-stranded amplified target nucleic acids useful in this invention can be increased. Using the methods described herein, one can uniquely identify a genomic sample by amplifying said target nucleic acids, isolating single-stranded amplified target nucleic acids, and determining the masses of said single-stranded amplified target nucleic acids using mass spectrometry. The resulting mass determination or mass spectrum will provide information which can be used to indicate a disease state, or propensity to disease, or to uniquely identify the source of the sample, or to map locations in a genome.

In yet another embodiment, methods are provided for detecting polymorphisms in at least one amplified target nucleic acid further comprising removing at least one flanking polynucleotide region, if present, from at least one of said amplified target nucleic acids before said isolating step.

In a further embodiment, methods for detecting polymorphisms are described wherein said isolating step comprises binding said amplified target nucleic acid to a solid support and said removing step comprises using one or more restriction endonucleases to cleave off one or more flanking polynucleotide regions.

The mass of a preferably single-stranded amplified target nucleic acid can be compared with the known or predicted mass of the corresponding wild type single-stranded amplified target nucleic acid that is the wild type version of the target nucleic acid that is being screened for polymorphism. Alternatively, the masses of more than one amplified target nucleic acid can be compared with the known or predicted masses of the corresponding wild type amplified target nucleic acids. The amplified target nucleic acid or set thereof, can optionally have one or more nucleotides replaced with mass-modified nucleotides, including mass-modified nucleotide analogs. Another optional aspect of the invention is the inclusion of internal calibrants or internal self-calibrants in the amplified target nucleic acid or set thereof to be analyzed by mass spectrometry to provide improved mass accuracy.

These above-described methods can also be combined with isolation methods designed to isolate a single-stranded amplified target nucleic acid or a set of single-stranded amplified target nucleic acids, for example, only those single-stranded target nucleic acids derived from the + or sense strand of the genome. The isolation methods include direct capture of one of the two strands of a double-stranded amplified target nucleic acid or set of such molecules, to a solid support or indirect capture of a single-stranded or double-stranded amplified target nucleic acid or set thereof to a solid support via a capture probe capable of binding to a solid support via covalent or noncovalent binding.

A further aspect of the invention includes the methods of detecting polymorphisms wherein said determining step optionally further comprises utilizing internal self-calibrants to provide improved mass accuracy. The isolation methods separately or together can also be combined with the use of internal self-calibrants.

The above methods, separately or in combination, can also be combined with the use of mass-modified nucleotides and mass-modified nucleotide analogs incorporated in the single-stranded or double-stranded amplified target nucleic acid or set of single-stranded or double-stranded amplified target nucleic acids to improve mass resolution between mass peaks. The methods of detecting polymorphisms may also include at least one single-stranded amplified target nucleic acid optionally having one or more nucleotides replaced with mass-modified nucleotides.

In another embodiment, kits for preparing amplified target nucleic acids for mass spectrometric analysis are also provided. The kits of the invention comprise a first primer capable of binding a first strand of one of said target nucleic acids at a region 5' to a region of interest of said target nucleic acid; a second primer capable of binding a second strand complementary to said first strand at a region 5' to said region of interest of said target nucleic acid; a DNA polymerase capable of extending said primers to form primer extension products of said first and second primers; wherein said first and second primers and said DNA polymerase are provided in a concentration and buffer suitable for increasing the number of target nucleic acids to form amplified target nucleic acids, and a restriction endonuclease capable of reducing length of amplified target nucleic acids. Another embodiment is a kit comprising: a first primer capable of binding a first strand of one of said target nucleic acids at a region 5' to a region of interest of said target nucleic acid; a second primer capable of binding a second strand complementary to said first strand at a region 5' to said region of interest of said target nucleic acid; a DNA polymerase capable of extending said primers to form primer extension products of said first and second primers; wherein at least one of said first or second primers is a cleavable primer.

DESCRIPTION OF SPECIFIC EMBODIMENTS

Figure 1A:
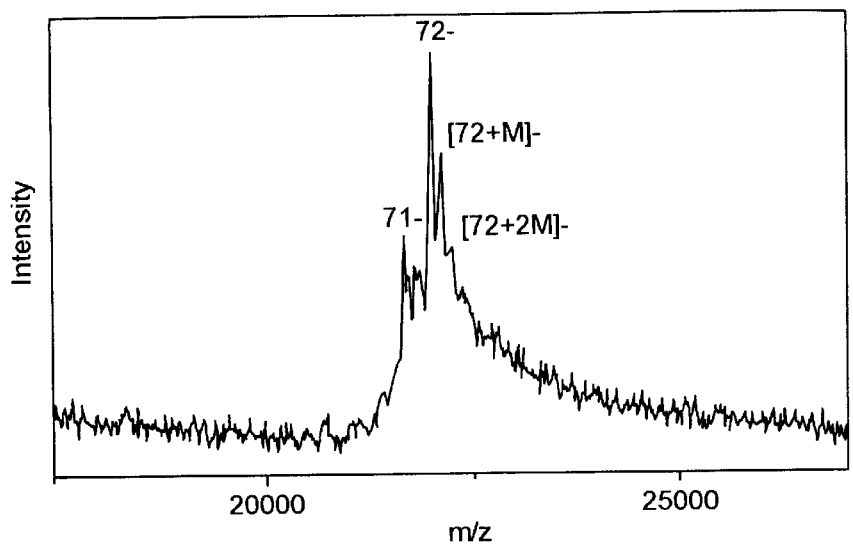
FIG. 1(a) and (b) display examples of resolved nucleic acid fragments (DNA) in the 20,000 to 30,000 Da range using MALDI-TOF mass spectrometry.

The present invention, directed to methods of preparing target nucleic acids for mass spectrometric analysis, provides the advantages of technical ease, speed, and high sensitivity (only minute samples of femtomole amounts are required). The methods described herein yield a minimal set of products with improved mass resolution and accuracy and detailed information about the nature of the polymorphisms detected in the target nucleic acids screened.

One embodiment of the present invention involves methods of detecting polymorphisms in one or more target nucleic acids comprising (a) amplifying at least one of said target nucleic acids, wherein each of said target nucleic acids comprises a region of interest and optionally one or more flanking regions, (b) isolating either a positive or a negative strand of interest of each of said target nucleic acids in the form of one or more single-stranded amplified target nucleic acids, wherein said isolating comprises binding said strand of interest of each of said amplified target nucleic acids to a solid support, and (c) determining the masses of each of said single-stranded amplified target nucleic acids using a mass spectrometer, wherein said determining does not involve sequencing of said amplified single-stranded target nucleic acids. The amplifying step can include the use of a specialized primer that can be used in the isolating step to bind the amplified target nucleic acids to a solid support. The primer can have attached a cleavable or reversible linker, or the primer itself may contain a cleavable site. If a cleavable site is introduced into one of said amplified target nucleic acids by using a cleavable or reversible linker during said amplifying step, the determining does not involve sequencing of said amplified target nucleic acids. The primer can be biotinylated or modified in other ways to effect binding of the amplified target nucleic acids to a solid support. The primer can optionally be bound to the solid support prior to amplified. One of ordinary skill in the art will appreciate the multiplicity of methods to effect such binding.

The isolating may further comprise denaturing and washing to remove the complementary strand from the strand of interest which has been bound to a solid support, followed by release of the bound single-stranded target nucleic acids from the solid support. Alternatively, the unbound complementary strand can be released and isolated for mass spectrometric analysis.

After amplifying and either before or after the amplified target nucleic acids have been bound to a solid support, the amplified target nucleic acid can be reduced in length by a number of different techniques. For example, one or more flanking regions can be cleaved off using one or more restriction endonucleases, which can include Type II or Type IIS restriction endonucleases or combinations thereof. An amplified target nucleic acid can also be reduced in length by using a cleavable primer. Another method of reducing length comprises using an exonuclease blocking moiety in one of the two primers for amplification, and digesting said amplified target nucleic acid with a 5'-3' exonuclease.

The target nucleic acid can be single-stranded or double-stranded DNA, RNA or hybrids thereof, from any source, preferably from a human source, although any source which one is interested in screening for polymorphisms can be used in the methods described herein. When the target nucleic acid is RNA, the RNA strand is the+strand. If desired, the target nucleic acid can be an RNA/DNA hybrid, wherein either strand can be designated the + strand and the other, the − strand. In cases where the amplified target nucleic acid contains RNA, the methods using restriction endonucleases described herein cannot be used to directly reduce the length of the final product. A restriction endonuclease can be used to reduce the length of the double-stranded DNA intermediates prior to the RNA transcription step. The target nucleic acid is generally a nucleic acid which must be screened to determine whether it contains a polymorphism. The corresponding target nucleic acid derived from a wild type source is referred to as a wild type target nucleic acid. The amplified target nucleic acids can be obtained from a source sample containing nucleic acids and can be produced from the nucleic acid by PCR amplification or other amplification techniques. The amplified target nucleic acids are typically less than 100 bases in length because current mass spectrometric methods do not have the mass accuracy and resolution necessary to identify a single base change in polynucleotides larger than 100 base pairs. However, as mass spectrometric techniques for analyzing nucleic acids improve, the single-stranded or double-stranded amplified target nucleic acids of this invention can be larger than 100 bases in length.

Due to the simpler mass spectrum that results from mass analysis of single-stranded amplified target nucleic acids, it is preferred to determine the masses of sets of single-stranded amplified target nucleic acids. The amplified target nucleic acids can also contain mass-modified nucleotides, which can enhance ease of analysis, especially when a point polymorphism has resulted in a very small mass change (on the order of 9 Da) in a target nucleic acid as compared to the corresponding wild type target nucleic acid. The methods described herein use mass spectrometry to determine the masses of a single-stranded amplified target nucleic acid or set of single-stranded amplified target nucleic acids to detect polymorphisms in at least one target nucleic acid.

The amplified target nucleic acids comprise a region of interest and optionally, one or more flanking regions, referred to as flanking regions. A region of interest contains or is suspected of containing a polymorphism, whereas a flanking region is generally believed not to contain a polymorphism or a polymorphism in that region is considered unimportant. The region of interest can be as small as a single nucleotide. A flanking region can contain a cleavable site or cleavable moiety that can be selectively cleaved to release single-stranded nucleic acids from a solid support prior to mass spectrometric analysis. An amplified target nucleic acid can also optionally comprise another flanking region on the end of the target nucleic acid opposite from the cleavable site used for release from the solid support. This second flanking region may contain one or more restriction cleavable sites that do not occur in the region of interest.

The methods described herein can be performed on a single amplified target nucleic acid or on a set of different amplified target nucleic acids, each containing a different region of interest. The various steps of reducing length, binding to a solid support, releasing from the solid support can differ with respect to each different target nucleic acid in a set, or can be the same, and the resulting set of single-stranded or double-stranded amplified target nucleic acids can be mass analyzed simultaneously. Accordingly, another advantage of the methods described herein is that they can be used to prepare a set or collection of two or more different target nucleic acids in a single reaction or a single container, possibly using at least one common reagent, which results in increased efficiency and more informative data from a single mass spectrum of the prepared target nucleic acids.

Wild type refers to a standard or reference nucleotide sequence, or number of repeat di-, tri-, or tetra-nucleotides, to which variations are compared. As defined, any variation from wild type is considered a polymorphism, including naturally occurring sequence polymorphisms, and mutations which are pathogenic.

The term complementary refers to the formation of sufficient hydrogen bonding between two nucleic acids to stabilize a double-stranded nucleotide sequence formed by hybridization of the two nucleic acids.

The types of mass spectrometry used in the invention include ESI or MALDI, wherein these methods may optionally include time-of-flight. The significant multiple charging of molecules in ESI and the fact that complex mixture analysis is often required mean that the ESI mass spectra will consist of a great many spectral peaks, possibly overlapping and causing confusion. Because the MALDI MS approach produces mass spectra with many fewer major peaks, this method is preferred. A MALDI MS time-of-flight instrument is preferred for the mass analysis of the invention.

The methods described herein do not require sequencing of one or more target nucleic acids (using the sequencing methods that require four different base-specific chain termination reactions or chemical cleavages to determine the complete nucleotide sequence of a nucleic acid) in order to determine the nature and presence of a polymorphism within any of said target nucleic acids. However, the methods described herein, separately or in combination, may be used in sequencing of one or more amplified target nucleic acids using mass spectrometric techniques.

For an initial polymorphism screen, a useful range of amplified target nucleic acid sizes that will allow detection of a point polymorphism is around 10 to 100 bases. This size range is where mass spectrometry presently has the necessary level of mass resolution and accuracy. Thus, the methods used in this invention are designed to produce amplified target nucleic acids ranging up to 100 bases in size, but can also be used to produce larger amplified target nucleic acids.

Existing mass spectrometric instrumentation in the case of MALDI-TOF MS optimally has a mass accuracy of about 1 part in 10,000 (0.01%), four times what is necessary for detecting a single base change in a 50-base long single-stranded DNA fragment. Utilization of mass-modified nucleotides (described herein) and nearby masses as internal calibrants, provides optimal resolution and mass accuracy of larger nucleic acids, and can extend the usable point polymorphism detection range up to 100 bases, if not higher. Continued advances in mass spectrometric instrumentation will also push this range higher.

Figure 1B:
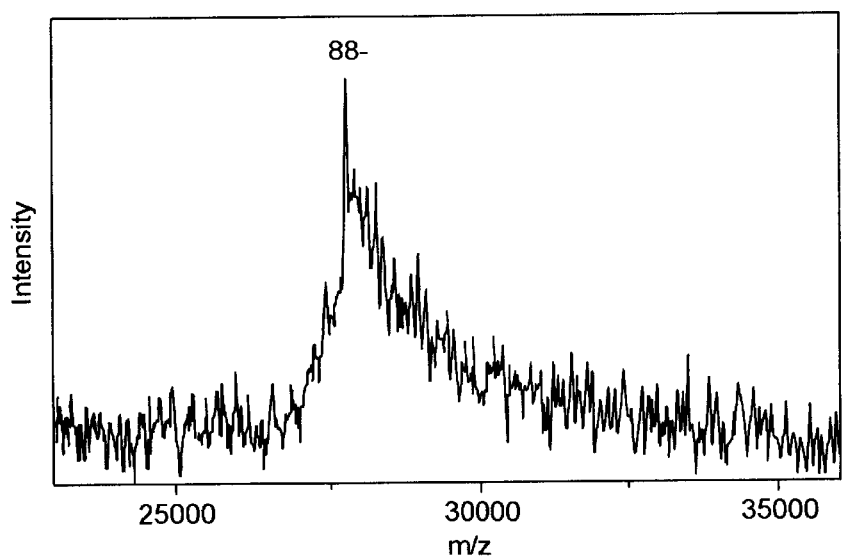

Examples of the resolving capabilities of MALDI-TOF MS are displayed in FIG. 1. FIG. 1 shows the positive ion TOF mass spectra obtained from 200 fmoles of DNA in the matrix 3-HPA. The top figure shows two single-stranded PCR products of lengths 71 and 72 (mass difference=305 Da=Adenosine) as well as the 72 mer and 72 mer + a single matrix adduct (M) (mass difference=139 Da) to be well resolved (FWHM resolution=240). The bottom figure shows an 88 base length single-stranded product having a resolution of 330. Both spectra display high enough accuracy and resolution to detect a point polymorphism if one were present.

These unique properties of mass spectrometry, MALDI-TOF MS in particular, to separate different amplified single-stranded target nucleic acids and identify their mass exactly and the methods taught herein provide novel methods for the screening of target nucleic acids and identification of changes in base composition that might result from genetic polymorphism.

Benefits of Analyzing Single-Stranded Nucleic Acids

One object of this invention is the accurate determination of the masses of a single-stranded amplified target nucleic acid or a set of single-stranded amplified target nucleic acids and correlation of this data to the characterization of any polymorphism, if present. The embodiments of this invention include mass spectrometric determination of masses of the single-stranded amplified target nucleic acid or set of different single-stranded amplified target nucleic acids, as well as mass determination of a mass-modified, single-stranded by amplified target nucleic acid or set thereof. A preferred embodiment is to detect polymorphisms in an amplified target nucleic acid in single-stranded form, wherein the single-stranded amplified target nucleic acid(s) are derived from one of either the positive or the negative strand of the genome. The examples of single-stranded methods described herein focus on single-stranded amplified target nucleic acids derived from the positive strand.

Figure 3:
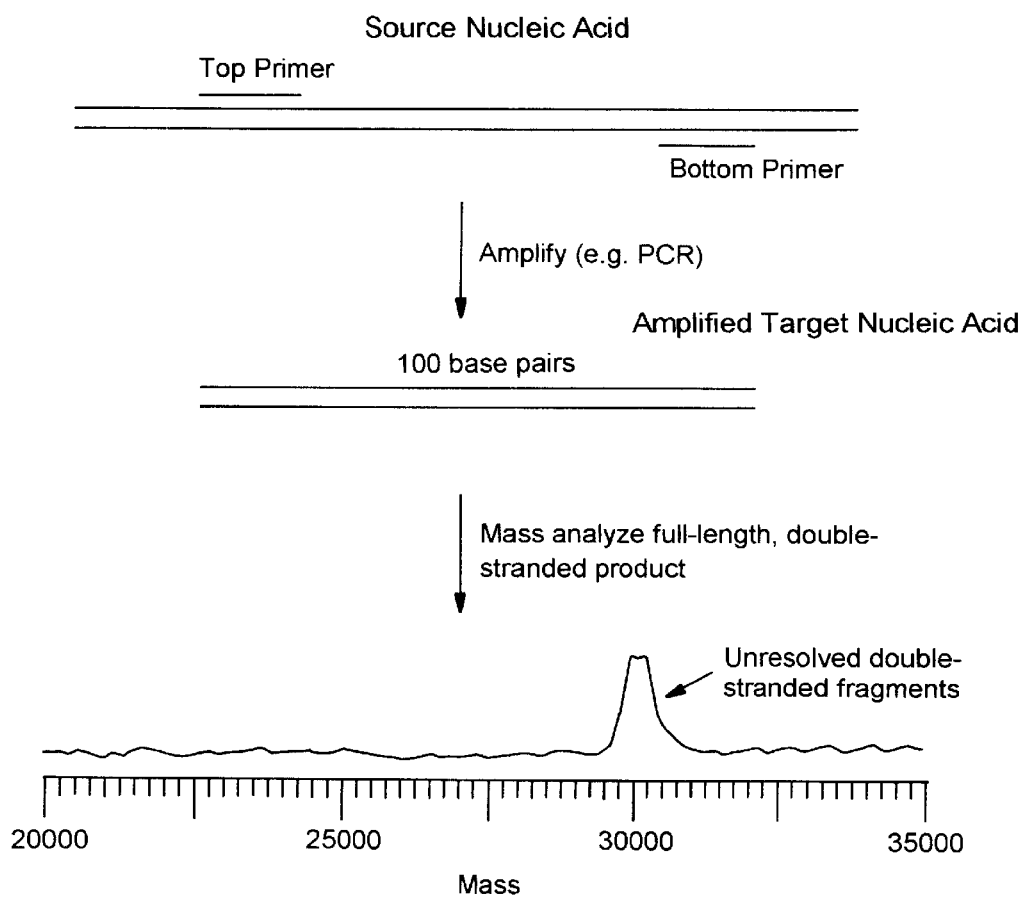
FIG. 3 is a diagram illustrating the effect of analyzing full-length double-stranded amplified target nucleic acid, where the blunt-ended double-strands result in unresolved peaks in the mass spectrum.

FIG. 3 illustrates that a double-stranded target nucleic acid comprising two complementary strands, produces two difficult to resolve peaks in the mass spectrum corresponding to the denatured single strands. The additional peaks from double-stranded amplified target nucleic acids as compared to single-stranded amplified target nucleic acids add to congestion of mass peaks in the mass spectra, as well as introducing the possibility that it may be extremely difficult, if not impossible, to resolve the complementary fragments if they have nearly or exactly identical base compositions. Furthermore, some portions of the double-stranded amplified target nucleic acids do not fully denature, and mass peaks corresponding to the double-stranded products increase the spectral congestion.

Spectra using both strands contain a two-fold redundancy in data, since any polymorphism in one strand will be present within its complement. Therefore, it is reasonable to remove one strand prior to mass spectrometric analysis and still produce all of the data necessary for complete polymorphism analysis. For these reasons, it is a preferred embodiment to analyze a set of single strands where only one of the two complementary sets of amplified target nucleic acids representing the full set of target nucleic acids is used.

Figure 4:
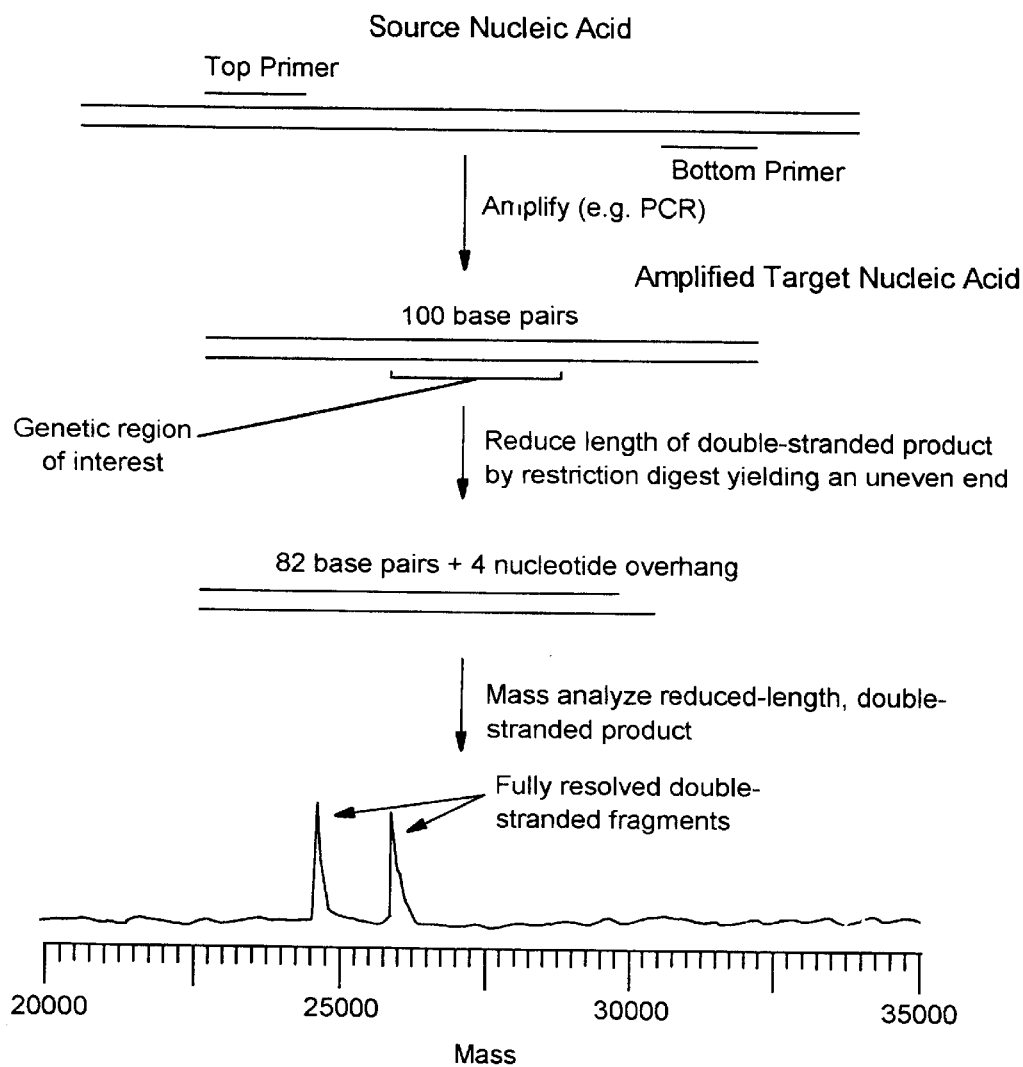
FIG. 4 is a diagram illustrating the effect of analyzing reduced-length double-stranded amplified target nucleic acid, where one of the strands has a 4 nucleotide overhang and results in fully resolved peaks in the mass spectrum.
Figure 5:
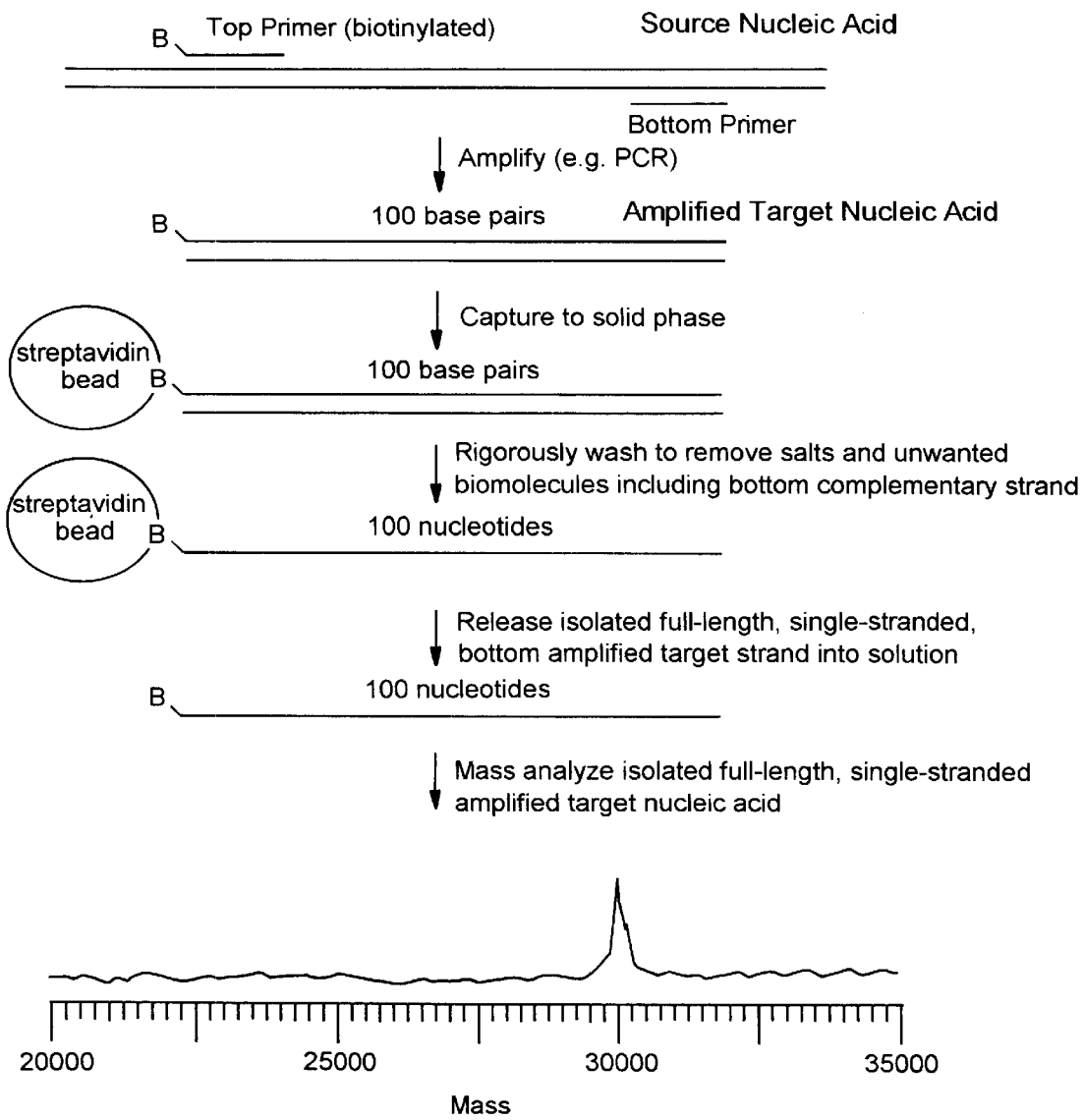
FIG. 5 is a diagram illustrating the effect of analyzing only a single-stranded amplified target nucleic acid in reducing the number of strands and simplifying the mass spectrum. This figure also illustrates release of the single-stranded amplified target nucleic acid by denaturing the streptavidin/biotin attachment to the solid support.
Figure 6:
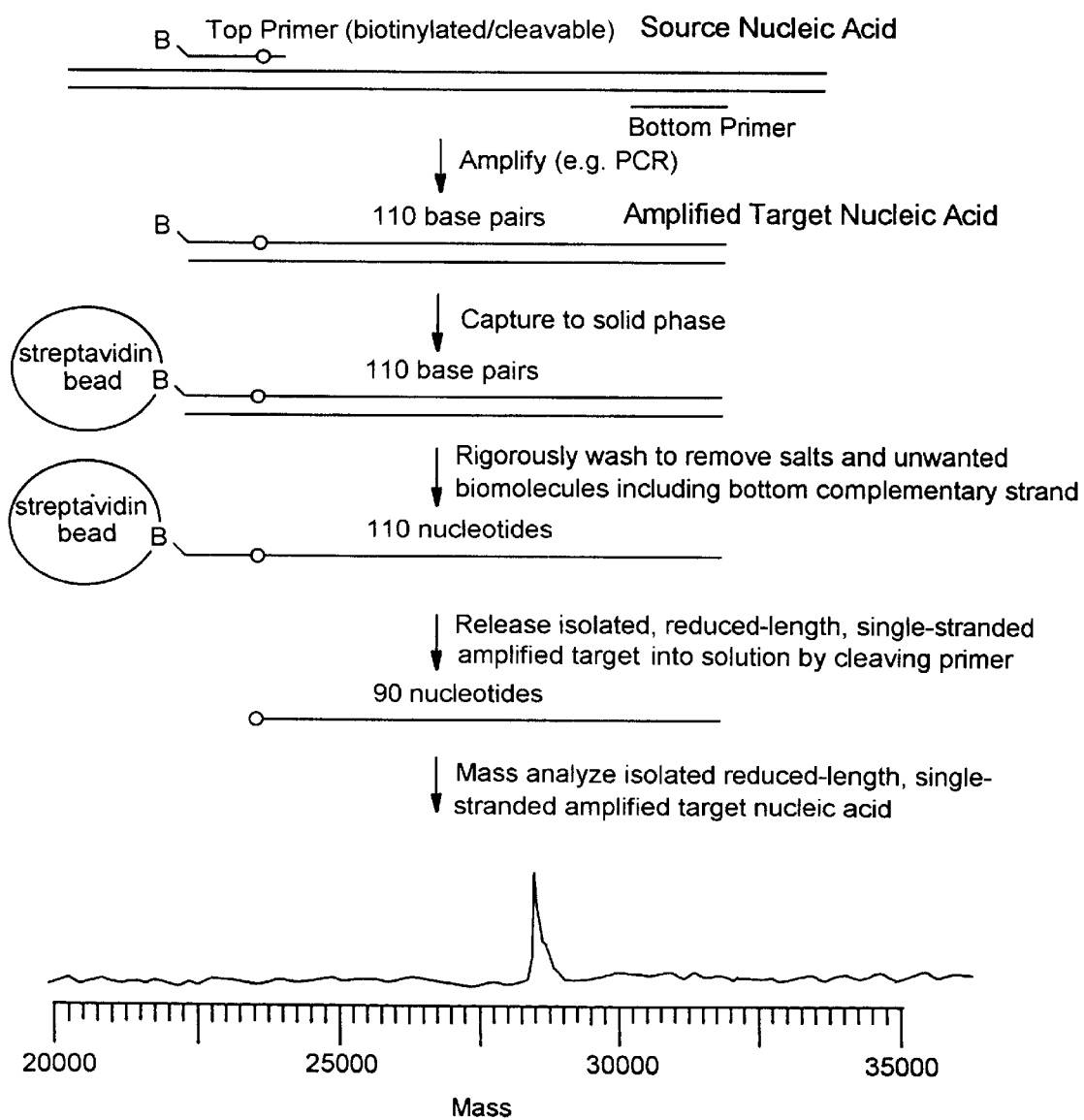
FIG. 6 is a diagram illustrating an amplified target nucleic acid that is larger than 100 base pairs that is reduced in length by cleaving a cleavable primer to release from the solid support a single-stranded amplified target nucleic acid of less than 100 nucleotides in length.

FIG. 4 shows the expected spectrum if only the positive strand of a target nucleic acid from FIG. 3 is analyzed by mass spectrometry. Analysis of one of the two complementary strands of the double-stranded amplified target nucleic acids halves the number of expected peaks within the mass spectra, allowing more total fragments to be resolved. Removal of one of the two strands from each amplified target nucleic acid eliminates the greatest source of complication for each spectra. A number of methods for isolating and preparing single-stranded amplified target nucleic acids for mass spectrometry are described herein.

Purification Methods

When analyzing target nucleic acids by mass spectrometry, there are several requirements that need to be met.

First, there is the need to produce target nucleic acids within the resolvable range and high mass accuracy range of the mass spectrometer.

Second, is to eliminate from the sample, nucleic acid fragments that do not contribute to the analysis and may unnecessarily convolute the mass spectra. With analysis methods such as gel electrophoresis, a mixture of specifically labeled nucleic acid fragments (radioactive or by fluorescent tagged) can be visualized in the presence of other unlabeled nucleic acid fragments that comigrate but are invisible and therefore do not convolute analysis of the gel data. The mass spectrometric methods described herein do not use any form of labeling that could render certain fragments invisible, e.g. the complementary strand in a double-stranded product, and it is therefore necessary to remove such fragments prior to analysis.

Third, is the need to produce samples of relatively high purity prior to introduction to the mass spectrometer. The presence of impurities, especially salts, greatly affects the resolution, accuracy and intensity of the mass spectrometric signal. Contaminating primers, residual sample genomic DNA, and proteins, all can affect the quality of the mass spectra.

In addition to the three requirements listed above it is also desirable for the methods to be amenable to automation, fast and inexpensive, providing an effective approach for detecting genetic polymorphisms.

The purification methods of the present invention are well-suited to mass spectrometric analysis of nucleic acids. For example, the methods herein physically isolate selected sets of single-stranded or double-stranded amplified target nucleic acids from a multiplicity of impurities including undesirable nucleic acid fragments (including the complementary strand and flanking regions), proteins, salts, that would result in a poor quality mass spectrum. These isolation methods offer significant advantages due to the physical separation of a desired set of single-stranded or double-stranded amplified target nucleic acids from other impurities in preparation.

Approaches of Isolating Single-Stranded or Double-stranded Amplified Target Nucleic Acids As described earlier, analysis of single-stranded amplified target nucleic acids is generally preferable since it provides a complete set of data with the minimal number of fragments and therefore simplifies the spectra and facilitates an increase in the total number of target nucleic acids that can be analyzed in a single assay. A number of approaches can be taken toward the production of single-stranded amplified target nucleic acids and their purification which includes the elimination of undesired oligonucleotides. In some cases, it may be preferable to use a method of amplification that yields primarily single-stranded amplified target nucleic acids, such as asymmetric PCR or transcription-mediated amplification.

To isolate the single-stranded amplified target nucleic acids, the amplified target nucleic acids may be designed to be attached or bound to a solid support. Several means are available to effect this attachment to a solid support, including: (a) hybridization to a complementary, solid-phase bound nucleic acid capture probe (which can be an oligonucleotide or one strand of the amplified target nucleic acid) comprising a first binding moiety that specifically binds to a second binding moiety attached to a solid phase; (b) direct binding of the amplified target nucleic acid strands of interest, each comprising a polynucleotide region of interest and a first binding moiety, to a second binding moiety attached to a solid phase (e.g. biotin/streptavidin or antigen/antibody pairs); or (c) direct covalent attachment of the strands of interest to a solid support.

A capture probe is an oligonucleotide that comprises a portion capable of hybridizing to a nucleic acid, such as an amplified target nucleic acid, and a binding moiety that binds the capture probe to a solid phase, either through covalent binding or affinity binding, or a mixture thereof. A capture probe can itself bind to a solid support via binding moieties (direct capture) or can bind to a solid support via another capture probe that binds to a solid support (indirect capture).

A preferred embodiment is the use of a biotinylated amplified target nucleic acid coupled to streptavidin attached to a solid support where the strand of interest is itself bound. Biotin coupling to streptavidin (or avidin) requires that any amplified target nucleic acid or acids contain a biotin. The biotin is part of the linker molecule. It is straightforward to capture the amplified target nucleic acid because biotinylated primers can be used in the PCR amplification. Because only one of the two strands of an amplified target nucleic acid is to be analyzed by mass spectrometry, only one of the two PCR primers for each different target nucleic acid should be biotinylated. For each target nucleic acid, the PCR primer to be biotinylated should be the primer that is extended to form the single-stranded amplified target nucleic acid of interest.

The amplified target nucleic acid or set of amplified target nucleic acids can be covalently attached to a solid support using any of the number of methods commonly employed in the art to immobilize an oligonucleotide or polynucleotide on a solid support. The amplified target nucleic acid or set of amplified target nucleic acids covalently attached to the solid support should be stable and accessible for base hybridization.

Covalent attachment of the amplified target nucleic acid or set of amplified target nucleic acids to the solid support may occur by reaction between a reactive site or a binding moiety on the solid support and a reactive site or another binding moiety attached to the target or via intervening linkers or spacer molecules, where the two binding moieties can react to form a covalent bond. Coupling of an amplified target nucleic acid or set of amplified target nucleic acids to a solid support may be carried out through a variety of covalent attachment functional groups. Any suitable functional group may be used to attach the amplified target nucleic acid or a set of amplified target nucleic acids to the solid support, including disulfide, carbamate, hydrazone, ester, N-functionalized thiourea, functionalized maleimide, mercuric-sulfide, gold-sulfide, amide, thiolester, azo, ether and amino.

The solid support may be made from the following materials: cellulose, nitrocellulose, nylon membranes, controlled-pore glass beads, acrylamide gels, polystyrene, activated dextran, agarose, polyethylene, functionalized plastics, glass, silicon, aluminum, steel, iron, copper, nickel and gold. Some solid support materials may require functionalization prior to attachment of an oligonucleotide or capture probe. Solid supports that may require such surface modification include aluminum, steel, iron, copper, nickel, gold, silicon, and nonfunctionalized polymers. Solid support materials for use in coupling to a capture probe include functionalized supports such as the 1,1'-carbonyldiimidazole activated supports available from Pierce (Rockford, Ill.) or functionalized supports such as those commercially available from Chiron Corp. (Emeryville, Calif.). Binding of an amplified target to a solid support can be carried out by reacting a free amino group of an amino-modified target with the reactive imidazole carbamate of the solid support. Displacement of the imidazole group results in formation of a stable N-alkyl carbamate linkage between the amplified target and the support.

The amplified target nucleic acid or a set of amplified target nucleic acids may also be bound to a solid support comprising a gold surface. The amplified target nucleic acid or set of amplified target nucleic acids can be modified at their 5'-end with a linker arm terminating in a thiol group, and the modified amplified target nucleic acid or set of modified amplified target nucleic acids can be chemisorbed with high affinity onto gold surfaces (Hegner, et al., Surface Sci. 291:39–46 (1993b)).

In all of the methods in which a solid-phase approach is used, the double-stranded amplified target nucleic acid or set of amplified target nucleic acids can be washed to remove deleterious contaminants. However, when the amplified target nucleic acid strands of interest are directly bound, either covalently or via biotin/streptavidin, it is possible to rigorously wash the sample to yield the highest purity. Such a rigorous wash typically removes the complementary strand, if present, isolating the single-stranded amplified target nucleic acid. Following washing, it is necessary to release single-stranded amplified target nucleic acids from the solid support for mass spectrometric analysis. The isolation of a set of single-stranded amplified target nucleic acids may be performed on the same plate that is used within the mass spectrometer or on a separate surface such as beads or a filter. Both the capture probe hybridization and biotin/streptavidin approaches can use a number of means of denaturation to disrupt the noncovalent interactions and afford release of the set of single-stranded amplified target nucleic acids bound to the solid support. Alternatively, a cleavable linkage can be incorporated between the first binding moiety and the amplified target nucleic acids. Any covalent coupling chemistry will need to be either reversible or it will be necessary to include a separate chemically cleavable linkage somewhere within the bound product. It may also be useful to use a chemically cleavable linkage approach with the biotin/streptavidin strategies so that release of the double-stranded target nucleic acids can be performed under relatively mild conditions. In all cases the cleavable linkage can be located within the linker molecule connecting the biotin and the base (e.g. a disulfide bond in the linker), within the base itself (e.g. a more labile glycosidic linkage), or within the phosphate backbone linkage (e.g. replacement of phosphate with a phosphoramidate).

Another way to isolate single-stranded amplified target nucleic acids is to use a primer comprising an exonuclease blocking moiety and to treat with a 5'-3' exonuclease, which digests the strand lacking an exonuclease blocking moiety and the portion of the other strand up to the exonuclease blocking moiety, leaving just the portion of the strand containing the exonuclease blocking moiety and the portion of that strand 3' to the exonuclease blocking moiety. This method is described in the methods of reducing length section herein. Single-stranded amplified target nucleic acids can also be isolated by using a DNA-specific or RNA-specific nuclease to digest an RNA/DNA hybrid.

The use of two primers each comprising an exonuclease blocking moiety, wherein each primer binds to a different complementary strand, is another way to isolate a double-stranded amplified target nucleic acid.

Methods of Reducing Length of Amplified Target Nucleic Acids

After the amplification of target nucleic acids, the amplified target nucleic acids, which are in double-stranded form, can be cleaved with restriction endonucleases to remove flanking regions that are not within the region of interest, wherein said region of interest is suspected of containing a polymorphism.

If DNA restriction endonucleases are used to remove one or more flanking regions from an amplified target nucleic acid prior to isolating the single-stranded or double-stranded amplified target nucleic acid(s), it is necessary that the amplified target nucleic acid have a double-stranded form prior to restriction, or more specifically, that the restriction endonuclease recognition sites and cleaving sites be located in double-stranded DNA regions flanking or outside the region of interest. The alternative to having fully double-stranded DNA prior to restriction is to hybridize restriction site oligonucleotide probes to single-stranded DNA, wherein the restriction site oligonucleotide probes are complementary to the restriction sites for selected restriction endonucleases.

The basic known methods for DNA isolation—precipitation, dialysis, filtration and chromatography do not isolate single-stranded from double-stranded DNA. If these purification methods are employed, and it is desired to produce a single-stranded product, it is necessary to add a separate step where single-strand isolation is performed.

If restriction endonucleases are used to cleave off one or more regions from an amplified target nucleic acid, a preferred method for isolating single-stranded amplified target nucleic acids from these products is to use at least one biotinylated primer located at one end of an amplified target nucleic acid.

The production of reduced length amplified target nucleic acids can provide benefits of increased accuracy and resolution in the mass spectrometric analysis of even double-stranded amplified target nucleic acids. Double-stranded amplified target nucleic acids can have their length reduced in a similar manner to that used for processing single-stranded amplified target nucleic acids. Either endogenous restriction recognition sites outside the region of interest or primer-incorporated restriction recognition sites, as described below, or combinations thereof can be used. Endogenous restriction recognition sites are those that are found naturally within one or more flanking regions.

Figure 7:
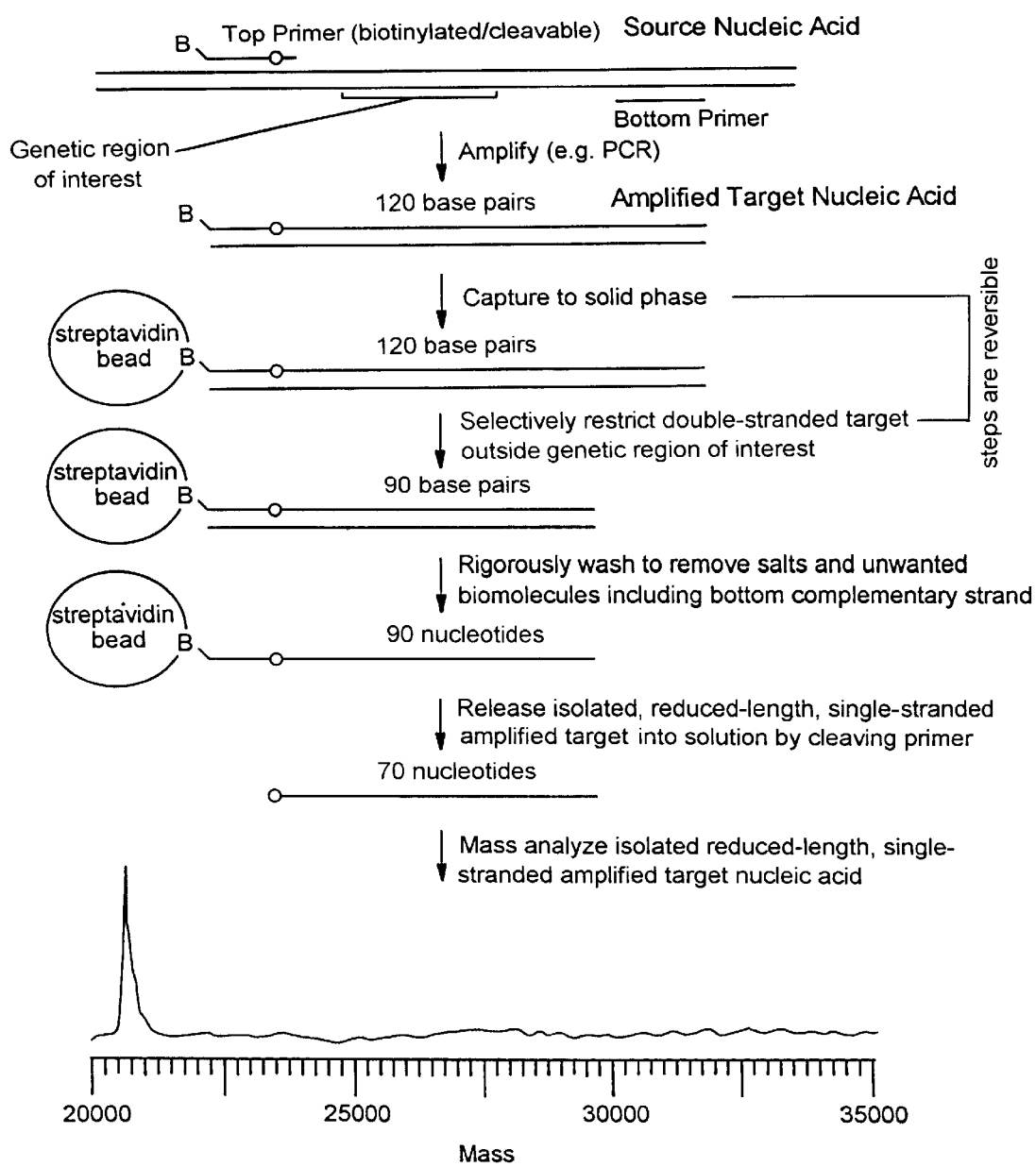
FIG. 7 is a diagram illustrating isolation of a single-stranded amplified target nucleic acid that has been reduced in length by cleaving off at least a portion of both flanking regions. The first flanking region contains a cleavable site in the cleavable primer, wherein the cleavable site is located outside of the region of interest. The second flanking region is on the opposite end of the amplified target nucleic acid and the portion of that second flanking region is cleaved off by digestion with a restriction endonuclease.

In cases where one or more endogenous restriction recognition sites cannot be found outside the region of interest, an alternative method is necessary for reducing the length of the amplified target nucleic acid. Use of a modified primer during the amplification process can mediate the incorporation of a Type II or Type IIS restriction endonuclease recognition site within a primer region of the amplified target nucleic acid. Type IIS restriction endonucleases recognize a particular double-stranded sequence region and selectively cleave the double strand a defined distance away from the recognition site. As an example, the restriction enzymes BpmI and BsgI cleave the double strands 14 nucleotides (top strand) and 16 nucleotides (bottom strand) away from the recognition sites. Other representative Type IIS restriction enzymes include BseRI, BsmRI and FokI. See New England Biolabs 1996 Product Catalog. Use of Type IIS restriction for the reduction of amplified target nucleic acids is illustrated in FIG. 7.

The restriction method for reducing the length of an amplified target nucleic acid does afford significant advantages even in cases where double-stranded amplified target nucleic acids are to be analyzed by mass spectrometry. For instance, the smaller molecules are easier to resolve. Moreover, a second beneficial effect of using restriction endonucleases to reduce length, specifically one that does not produce blunt ends, is the production of two strands of different lengths and hence different masses. The creation of two complementary strands of different lengths, e.g. 4 to 6 nucleotides difference in size, yields dramatically improved separation and resolution of two complementary strands during mass spectrometric analysis. See FIG. 4. In many cases, reduction of length by restriction endonuclease digestion can eliminate the need for single-strand isolation.

In one embodiment, the restriction endonuclease recognition site can be the same as the site of cleavage, located in the flanking region opposite from the end of the amplified target nucleic acid that is bound to the solid support. In another embodiment, the restriction endonuclease recognition site is different from the site of cleavage, as in the case of Type IIS restriction endonucleases, which cleave at a defined distance (20–40 bases) from one side of their recognition sequence. When a Type IIS restriction endonuclease is used to reduce the length of an amplified target nucleic acid, both the recognition site and the site of cleavage are commonly located outside of the region of interest and in the flanking region.

One of ordinary skill will readily appreciate that many combinations and variations of these methods for reducing length are possible. For example, endogenous Type II restriction recognition sites for one or more Type II restriction endonucleases can be used to reduce length on one or both regions flanking a region of interest. Alternatively, endogenous Type II and endogenous Type IIS restriction recognition and cleavage sites can be used to reduce length by cleaving in one or more flanking regions. Also, one or more restriction recognition sites can be introduced using a mismatch primer or an overhang primer containing one or more new restriction recognition sites. A mismatch primer is one which contains at least a single base mismatch with the target nucleic acid to be amplified and can include primers that have an overhang region that does not hybridize to the target nucleic acid. Mismatch primers are a type of cleavable primer. Alternatively, endogenous restriction recognition sites and primer-introduced restriction recognition sites can be combined. Cleavable sites can also occur outside the primer region, ranging from 20–50 nucleotides away from the end of the primer region. All of these types of primers are cleavable primers because they contain a site, moiety or group, that can be used to reduce the length of the target nucleic acid. For example, cleavable primers may contain a recognition site, a cleavable site, or an exonuclease blocking moiety.

Figure 9:
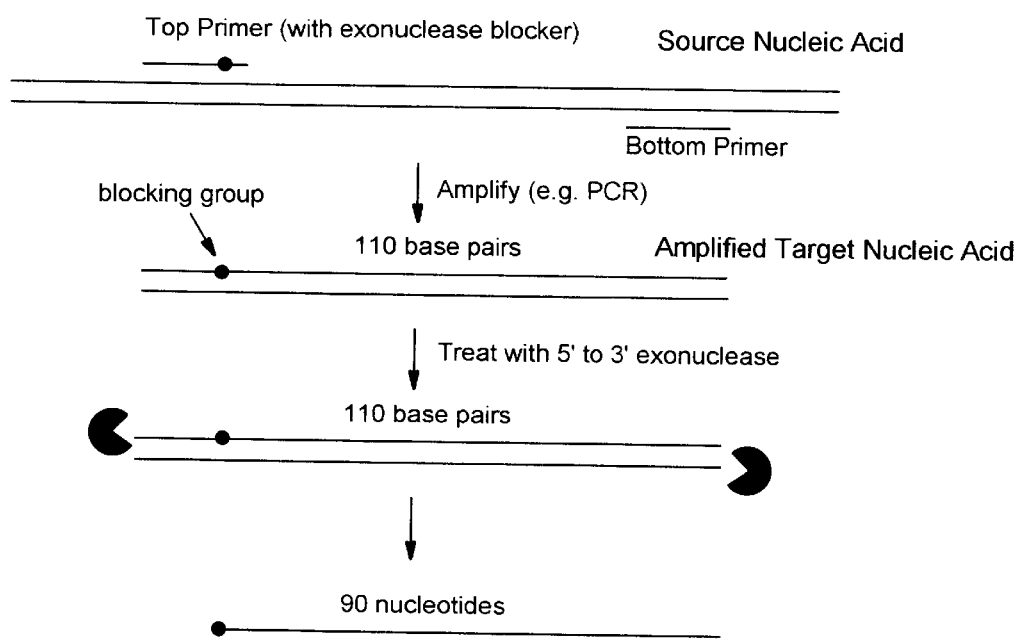
FIG. 9 is a diagram illustrating another embodiment of the invention, wherein a primer has an exonuclease blocker. After amplification of the target nucleic acid, the amplified target nucleic acid comprises an exonuclease blocking group. The amplified target nucleic acid is then treated with a 5' to 3' exonuclease, which degrades the strand containing the exonuclease blocking group only up to the blocking group. The 5' to 3' exonuclease completely degrades the other strand of the amplified target nucleic acid, wherein the other strand does not have an exonuclease blocking group. The treatment with the 5' to 3' exonuclease leaves a single stranded amplified target nucleic acid for mass spectrometric analysis.
Figure 10:
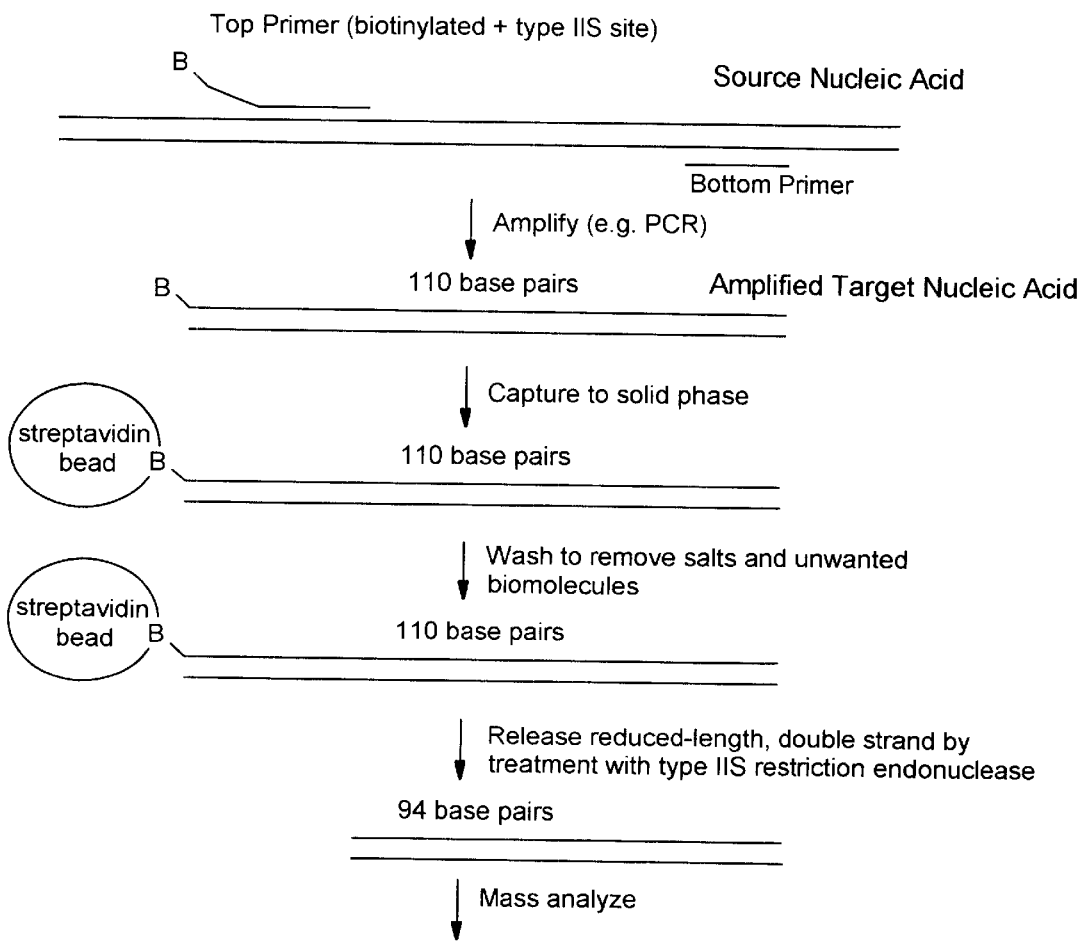
FIG. 10 is a diagram illustrating yet another embodiment, in which one primer comprises a Type IIS restriction recognition site and a binding moiety, e.g., biotin, wherein the Type IIS restriction site of cleavage is located between the Type IIS restriction recognition site and the binding moiety. The source nucleic acid is then amplified using this primer and another primer complementary to the other strand. The amplified target nucleic acid is then restricted with the Type IIS restriction endonuclease corresponding to the Type IIS restriction recognition and cleavable sites in the primer, leaving a reduced-length amplified target nucleic acid comprising a binding moiety, e.g. biotin, which can then be captured to a solid phase. The reduced-length amplified target nucleic acid is then rigorously washed to remove salts and the unbound complementary strand. Then the reduced-length, single-stranded amplified target nucleic acid is then released from the solid support for mass spectrometric analysis.
Figure 11:
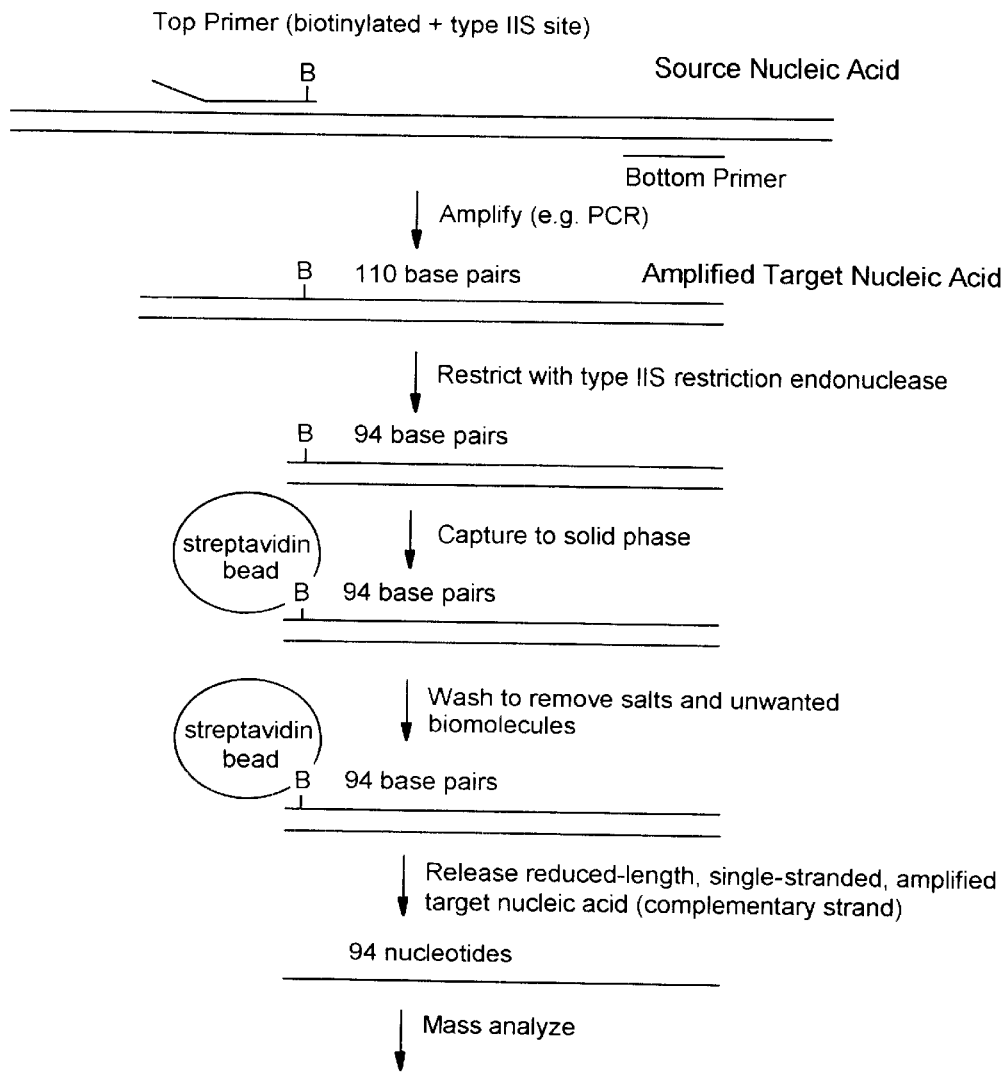
FIG. 11 is a diagram illustrating a variation of the embodiment illustrated in FIG. 10, wherein instead of isolating the bound reduced-length, single-stranded amplified target nucleic acid, the complementary (unbound) strand is released from the bound strand and isolated for mass spectrometric analysis.
Figure 12:
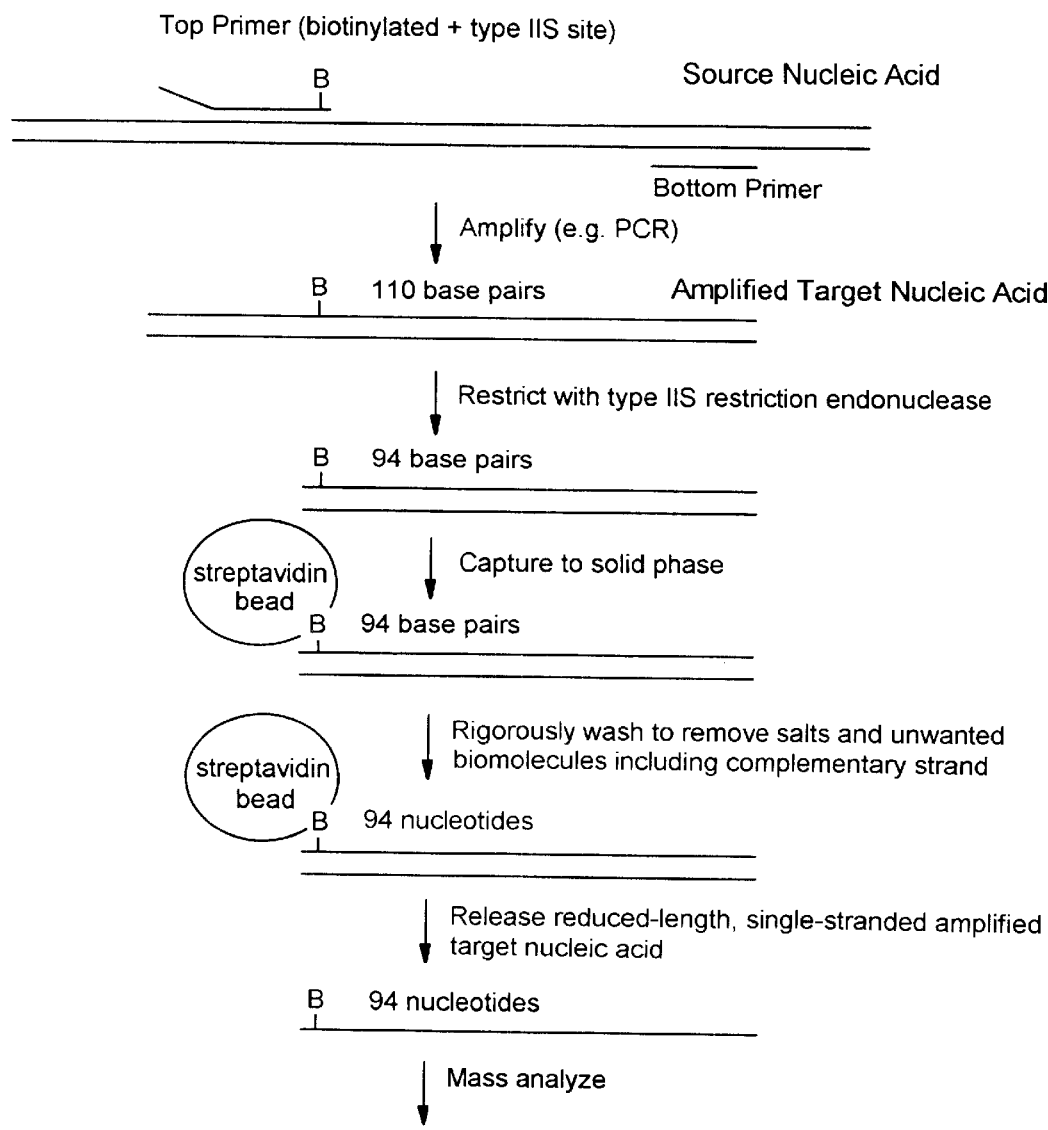
FIG. 12 is a variation of FIG. 11, wherein a double-strand nucleic acid is analyzed by mass spectrometry and wherein the recognition site is located between the binding moiety and the region of interest.

Another method of reducing length involves the use of a primer comprising an exonuclease blocking moiety, wherein said exonuclease blocking moiety prevents a 5-3' exonuclease from digesting a region of interest that is 3' to said exonuclease blocking moiety. The exonuclease blocking moiety can include modified nucleotides that prevent 5'-3' exonuclease activity from continuing, e.g.

phosphorothioates, methyl phosphonates, borano phosphates, and peptide nucleic acids (PNA). FIG. 9 is an example of the use of an exonuclease blocking moiety and an exonuclease to reduce the length of a target nucleic acid. The nucleotides that are degraded by the exonuclease are a multiplicity of cleavable sites, including many that are adjacent to one another.

Figure 8:
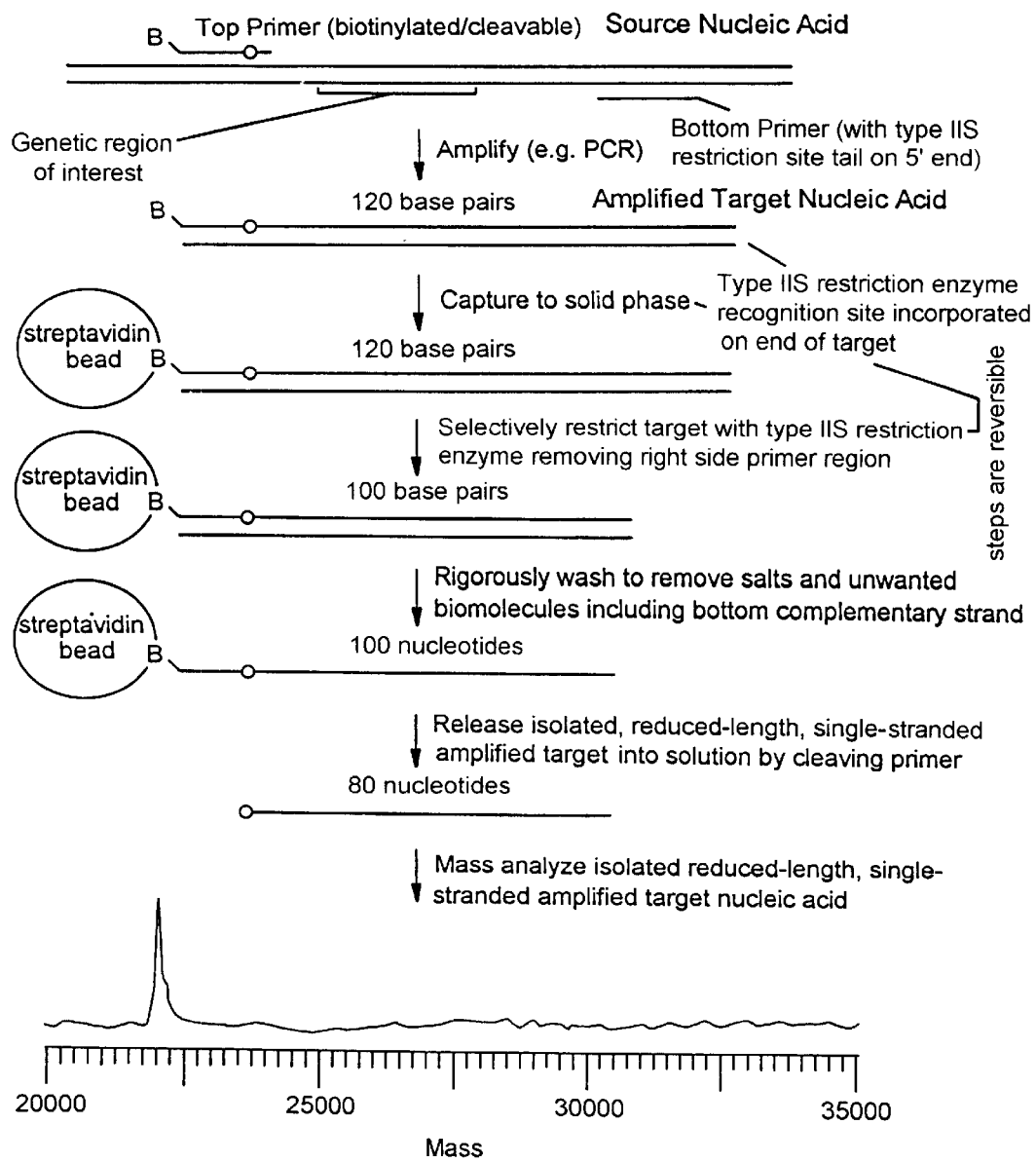
FIG. 8 is a diagram illustrating isolation of a single-stranded amplified target nucleic acid, where the length of the amplified target nucleic acid is reduced by cleaving off a portion of both flanking regions by (1) using a primer having a chemically cleavable site incorporated during amplification; (2) using a primer having a Type IIS restriction endonuclease recognition site during amplification; (3) cleaving off one flanking region by digesting with said Type IIS restriction endonuclease; and (4) after rigorously washing to remove salts and unwanted biomolecules, including the unwanted (unbound) complementary strand, releasing the single-stranded amplified target nucleic acid from said solid support by cleaving at said cleavable site within the cleavable primer.

Peptide nucleic acids are modified DNA mimics in which the sugar-phosphate backbone has been replaced with a backbone based on amino acids. Peptide nucleic acids exhibit sequence-specific binding to DNA and RNA and are resistant to nuclease and protease attack. See O. Buchardt et al., Trends Biotechn., 11(9): 384–386 (1993). A preferred 5'-3' exonuclease is Exonuclease III. FIG. 8 illustrates how the use of this method results in isolation of a reduced-length single-stranded amplified target nucleic acid.

The exonuclease approach to reducing length can be used in combination with one or more of the restriction endonuclease cleavage techniques described above to reduce length. In such a combined approach, the restriction cleavage should occur before the exonuclease digestion.

One of ordinary skill in the art will appreciate that the above methods of reducing length may also be used as means of isolating a reduced-length amplified target nucleic acid or a reduced-length single-stranded amplified target nucleic acid. For example, a chemically cleavable site can be incorporated in a flanking region and cleavage at that site can accomplish both length reduction and release from a solid support at the same time.

For example, after the amplified target nucleic acid is reduced in length, either the bound strand or the unbound strand or both strands of said amplified target nucleic acid can be isolated for mass spectrometric analysis.

In cases where the single-stranded amplified target nucleic acid strand to be analyzed is directly bound to the solid phase, it can be rigorously washed to remove unbound components, including any number of deleterious contaminants, including the unwanted complementary strand, nucleic acid fragments containing at least a portion of a flanking region, salts, enzymes, and other reagents. These unbound components can be removed from any nucleic acid bound to a solid support in any of the embodiments described herein and combinations thereof. If the strand to be analyzed (the strand of interest) is not bound directly but rather via hybridization to a complementary nucleic acid, it cannot be as rigorously washed and thereby cannot be purified to as great an extent. Direct binding of the amplified target nucleic acid strand to be analyzed ultimately produces a higher quality signal, e.g. less salt adducts, during mass spectrometric analysis, thus improving mass resolution and accuracy.

Following the necessary wash steps, the single-stranded amplified target nucleic acids are released from the solid support and analyzed by mass spectrometry. Note that regions that are cleaved off by one or more restriction endonucleases are released into solution and washed away, and are therefore not analyzed. Loss of these flanking regions can enhance the ability for mass spectrometry to quickly identify the existence of a polymorphism. The isolation of the single-stranded amplified target nucleic acids occurs prior to the mixing of the single-stranded amplified target nucleic acids with the matrix material for mass spectrometric analysis.

To release the reduced-length single-stranded amplified target nucleic acid from the solid support, several methods can be used, depending on the methods used to bind the amplified target nucleic acid to the solid support. Both the hybridization and biotin/streptavidin methods can use a number of means of denaturation to disrupt noncovalent interactions and cause the release of the bound single-stranded amplified target nucleic acids. Any covalent chemistry used must be either reversible or include a separate chemically cleavable site somewhere within the bound product. It may be preferred to use a chemically cleavable site with the biotin/streptavidin method so that release of the target nucleic acids can be performed under relatively mild conditions. In all cases, the cleavable site can be located within a linker molecule connecting the biotin and the base (e.g. a disulfide bond in the linker), within the base itself (e.g. a more labile glycosidic linkage), or within the phosphate backbone linkage (e.g. replacement of phosphate with a phosphoramidate).

In a preferred embodiment, the cleavable site is located near the 3' end of the primer used to bind the amplified target nucleic acid to the solid support. By locating the cleavable site near the 3' end, it is possible to further reduce the length of the amplified target nucleic acid, eliminating a flanking region from the polynucleotide region of interest. Cleavable primers are described in PCT/US96/06116, filed Apr. 26, 1996 (incorporated herein by reference).

Improving Mass Accuracy by Internal Calibration and Internal Self-calibration

Mass spectrometers are typically calibrated using analyses of known mass. A mass spectrometer can then analyze an analyte of unknown mass with an associated mass accuracy and precision. However, the calibration, and associated mass accuracy and precision, for a given mass spectrometry system (including MALDI-TOF MS) can be significantly improved if analyses of known mass are contained within the sample containing the analyte(s) of unknown mass(es). The inclusion of these known mass analyses within the sample is referred to as use of internal calibrants. External calibrants, i.e. analyses of known mass that are not mixed in with the set of target nucleic acids of unknown mass and simultaneously analyzed in a mass spectrometer, are analyzed separately. External calibrants can also be used to improve mass accuracy, but because they are not analyzed simultaneously with the set of target nucleic acids of unknown mass, they will not increase mass accuracy as much as internal calibrants do. Another disadvantage of using external calibrants is that it requires an extra sample to be analyzed by the mass spectrometer. For MALDI-TOF MS, generally only two calibrant molecules are needed for complete calibration, although sometimes three or more calibrants are used. All of the embodiments of the invention described herein can be performed with the use of internal calibrants to provide improved mass accuracy.

Using the methods described herein, one can obtain a mass spectrum with numerous mass peaks corresponding to the set of single-stranded amplified target nucleic acids under study. If no polymorphism is present in any of said target nucleic acids, all of the mass peaks corresponding to the amplified target nucleic acids will be at mass-to-charge ratios associated with the set of amplified target nucleic acids from the wild type target nucleic acids. However, if a target nucleic acid contains a polymorphism, usually no more than one or two of the mass peaks will be shifted in mass, leaving the majority of mass peaks at unaltered locations. In a preferred embodiment of the invention, a self-calibration algorithm uses these nonpolymorphic or unmutated target nucleic acids for internal calibration to optimize the mass accuracy for analysis of the single-stranded amplified target nucleic acids containing a polymorphism, thus requiring no added calibrant(s), simplifying the calibration, and avoiding potential spectral overlaps. In a given sample, however, it will not be known a priori which mass peaks, if any, are altered or shifted from their expected masses for the wild type target nucleic acids.

The self-calibration algorithm begins by dividing up the observed mass peaks into subsets, each subset consisting of all but one or two of the observed mass peaks. Each data subset has a different one or two mass peaks deleted from consideration. For each subset, the algorithm divides the subset further into a first group of two or three masses which are then used to generate a new set of calibration constants, and a second group which will serve as an internal consistency check on those new constants. The internal consistency check begins by calculating the mass difference between the m/z values calculated for the second group of mass peaks and the values corresponding to reasonable choices for the associated wild-type target nucleic acids. The internal consistency check can thus take the form of a chi-square minimization where the key parameter is this mass difference. The algorithm finds which data subset has the lowest sum of the squares of these mass differences resulting in a choice of optimized calibration constants associated with group one of this data subset.

After new self-optimized calibration constants are obtained, the mass-to-charge ratios are determined for the mass peaks omitted from the data subset; these are the amplified target nucleic acids suspected to contain a polymorphism. The differences from the observed mass peaks for the wild type amplified target nucleic acids are then used to determine whether a polymorphism is present, and if so, what the nature of this polymorphism is (e.g. the exact type of deletion, insertion, or point polymorphism). This self-calibration procedure should yield a mass accuracy of approximately 1 part in 10,000.

The methods described herein permit MALDI-TOF MS analysis of single-stranded amplified target nucleic acids which has a mass accuracy of approximately 1 part in 10,000. The use of internal self-calibrants makes it possible to extend this level of accuracy up to and potentially beyond 30,000 Da or 100 bases. This mass accuracy enables exact sizing of one or more target nucleic acids and the determination of the presence and nature of any polymorphism, including point polymorphisms, insertions and deletions. Further described herein are methods for improving the resolution of individual target nucleic acids by means including elimination of equal-length complementary pairs through the use single-strand-targeted isolation procedures, and the incorporation of mass-modified nucleotides to enhance the mass difference between similar sized amplified target nucleic acids and/or wild type amplified target nucleic acids. In addition, these methods provide for the removal of salts and other deleterious materials as well as a means for the removal of unwanted nucleic acid fragments prior to mass spectroscopic analysis.

Mass Resolution, Mass Accuracy, and the use of Mass-modified Nucleotides

Any of the embodiments of the invention described herein optionally include amplified target nucleic acids having one or more nucleotides replaced with mass-modified nucleotides, wherein said mass-modified nucleotides comprise nucleotides or nucleotide analogs having modifications that change their mass relative to the nucleotides that they replace. The mass-modified nucleotides incorporated into the target nucleic acids of the invention must be amenable to the enzymatic and nonenzymatic processes used for the amplification of target nucleic acids. For example, the mass-modified nucleotides must be able to be incorporated by DNA or RNA polymerase during amplification of the target nucleic acid. Moreover, the mass-modified nucleotides must not inhibit the processes used to process the target nucleic acids, including, inter alia, specific cleavage by restriction endonucleases, whenever such steps are used. Mass-modifications can also be incorporated in the target nucleic acids of the invention after the enzymatic steps have been concluded. For example, a number of small chemicals can react to modify specific bases, such as kethoxal or formaldehyde.

Any or all of the nucleotides in the target nucleic acids can be mass-modified, if necessary, to increase the spread between their masses. It has been shown that modifications at the C5 position in pyrimidines or the N7 position in purines do not prevent their incorporation into growing nucleic acid chains by DNA or RNA polymerase. L. Lee et al. "DNA Sequencing with Dye-Labeled Terminators and T7 DNA Polymerase: Effect of Dyes and dNTPs on Incorporation of Dye-Terminators and Probability Analysis of Termination Fragments" Nuc. Acids. Res. 20, 2471 (1992). For example, an octynyl moiety can be used in place of methyl on thymidine to alter the mass by 94 Da.

Mass-modifying groups can be, for example, halogen, alkyl, ester or polyester, ether or polyether, or of the general type XR, wherein X is a linking group and R is a mass-modifying group. The mass-modifying group can be used to introduce defined mass increments into the target nucleic acids. One of skill in the art will recognize that there are numerous possibilities for mass-modifications useful in modifying nucleic acid fragments or oligonucleotides, including those described in Oligonucleotides and Analogues: A Practical Approach, Eckstein ed. (Oxford 1991) and in PCT/US94/00193, which are both incorporated herein by reference.

Figure 2:
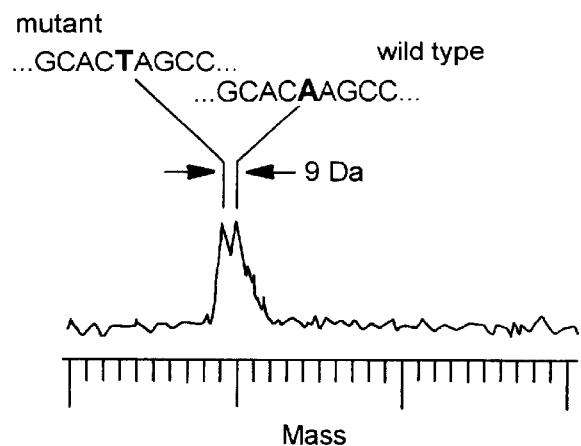
FIG. 2 illustrates the effect on mass resolution of a mass-substituted base where a T has been replaced by heptynyldeoxyuridine during amplification of the polymorphic region of interest.
Figure 2:
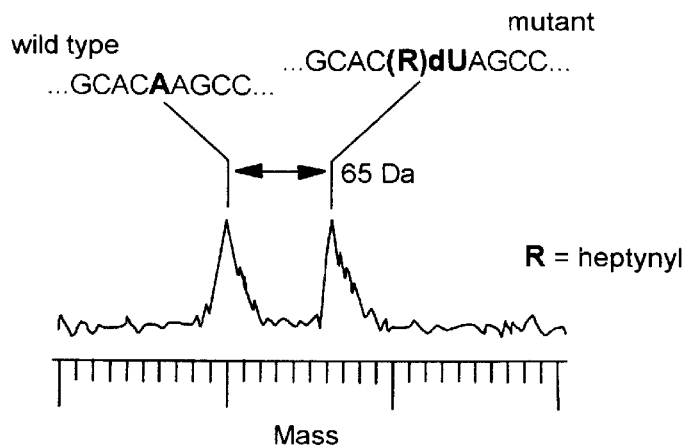

At larger mass ranges (30,000–90,000 Da), the mass resolution and mass accuracy of current MALDI-TOF mass spectrometers will not be sufficient to identify a single base change. For this reason, it may be preferable to increase the useful mass range artificially by substituting standard nucleotides within a target nucleic acid with mass-modified nucleotides having significantly larger mass differentials. Use of mass-modified nucleotides applies as well to the mass range below 30,000 Da. Mass modification can generally increase the quality of the mass spectra by enlarging the mass differences between different amplified target nucleic acids of similar size and composition. For example, mass-modified nucleotides can increase the minimum mass difference between two amplified target nucleic acids that happen to be identical in base composition except for a single base which is an A in one and is a T in the other. Normally, these two target nucleic acids will differ in mass by only 9 Da. By replacing one of the bases with a mass-modified version during amplification, the mass difference can be >20 Da. The illustrations of spectra in FIG. 2 depict the influence mass-modified nucleotides can have on target nucleic acid resolution. One example of the many possible mass modifications useful in this invention is the use of 5-(2-heptynyl)-deoxyuridine in place of thymidine. The replacement of a methyl group by heptynyl changes the mass of this particular nucleotide by 65 Da. An A to T transversion in a nucleic acid in which all thymidine bases have been replaced with 5-(2-heptynyl)-deoxyuridine would produce a peak shift of 56 Da as opposed to 9 Da for the same nucleic acid fragments without the mass-modified nucleotides. The use of mass-modified nucleotides is especially important in the analysis of single-stranded target nucleic acids derived from RNA. Normally, the masses of C and U vary by only 1 Da, making it practically impossible to detect C to U or U to C point polymorphisms within a given target nucleic acid.

Each of the techniques described herein can be used in combination with any of the isolation methods also described herein. Moreover the techniques can be used in combination with each other, as one of ordinary skill in the art using the techniques described herein how to combine the different aspects of the invention. All of these methods and combinations thereof can optionally include use of mass-modified nucleotides and internal calibrants.

Kits

The present invention also includes kits for preparing nucleic acids for mass spectrometric analysis. In one embodiment, a kit comprises: a first primer capable of binding a first strand of one of said target nucleic acids at a region 5' to a region of interest of said target nucleic acid; a second primer capable of binding a second strand complementary to said first strand at a region 5' to said region of interest of said target nucleic acid; a DNA polymerase capable of extending said primers to form primer extension products of said first and second primers; and a restriction endonuclease capable of reducing length of amplified target nucleic acids. The restriction endonuclease can be a type II restriction endonuclease or a Type IIS. Either the first or second primer can be biotinylated, i.e. comprise at least one biotin. The kit can also comprise a solid support capable of selectively binding either a positive strand or a negative strand comprising the region of interest of aid amplified target nucleic acids, and a matrix solution.

In another embodiment, a kit comprises a first primer capable of binding a first strand of one of said target nucleic acids at a region 5' to a region of interest of said target nucleic acid; a second primer capable of binding a second strand complementary to said first strand at a region 5' to said region of interest of said target nucleic acid; a DNA polymerase capable of extending said primers to form primer extension products of said first and second primers; wherein at least one of said first or second primers is cleavable by chemical or enzymatic treatment. The cleavable primers of the invention include those comprising a chemically cleavable site, an exonuclease blocking moiety, a Type IIS restriction endonuclease recognition site, or at least one biotin, but does not include a Type II restriction endonuclease recognition site where one of the complementary strands cannot be cleaved by said Type II restriction endonuclease. This kit can optionally comprise a solid support and a matrix solution.

The following examples are provided to illustrate embodiments of the invention, but do not limit the scope of the invention.

EXAMPLES

Example 1

PCR Amplification of a Single Target Nucleic Acid

PCR methods have been extensively developed during the last decade. An example protocol is as follows. A sample containing 10–10,000 copies of a source DNA is mixed with two antiparallel DNA primers that surround a target nucleic acid, e.g. the coding region for a gene involved in carcinogenesis. The target nucleic acid can be any sequence that is known or suspected to be polymorphic, including short tandem repeats (STRs), simple sequence length polymorphisms (SSLP), and genetic deletions, insertions, or point polymorphisms. The PCR mix is composed of: 8 $\mu$l 2.5 mM deoxynucleoside triphosphates, 10 $\mu$l 10×PCR buffer, 10 $\mu$l 25 mM MgCl$_2$, 3 $\mu$l 10 $\mu$M forward primer, 3 $\mu$l 10 $\mu$M reverse primer, 0.3 $\mu$l thermostable Taq DNA polymerase, 64.7 $\mu$l H$_2$O, and 1 $\mu$l source DNA. The sample tube is sealed and placed into a thermal cycling device. A typical cycling protocol is as follows:

| Step 1 | 95° C. | 2 min. |
|---|---|---|
| Step 2 | 95° C. | 15 sec. |
| Step 3 | 55° C. | 15 sec. |
| Step 4 | 72° C. | 1 min. |
| Step 5 | repeat Steps 2–4 35 times | |
| Step 6 | 72° C. | 5 min. |
| Step 7 | stop | |

Example 2

Production of Single-Stranded Nucleic Acids by Asymmetric PCR

The basic PCR procedure can be modified in order to produce predominantly one of the two strands. These asymmetric procedures involve modifying the ratios of the two primers, a typical ratio is 10:1. These procedures are described in Molecular Cloning: A Laboratory Manual, pp. 14.28–14.29 (2d ed. 1989, Sambrook, Fritsch and Maniatis, eds.)(incorporated by reference herein)

Example 3

Production of Single-Stranded DNA via Biotinylated PCR Products

For the preparation of capturing amplified target nucleic acids to a solid support, one of the two primers used in PCR amplification can be synthesized with a biotin moiety internally or at the 5' end of the oligonucleotide. Following a standard PCR, the double-stranded product can be bound to a solid-phase surface coated with streptavidin. For example, 10 pmol of double-stranded PCR product is mixed with 5 $\mu$l of 10 mg/ml paramagnetic streptavidin-coated beads in a binding/washing buffer of 2.0 M NaCl, 10 mM TrisCl, 1 mM EDTA, pH 8.0. The solution is incubated for 15 min. at room temperature with mixing. Following incubation the tube is placed next to a high field, rare earth magnet and the paramagnetic beads with the bound biotinylated PCR product are precipitated to the wall of the tube. The supernatant is removed, and the particles, outside the influence of the magnetic field, are resuspended into binding/washing buffer. The beads and wash solution are mixed and then subjected once again to the magnetic field to precipitate the magnetic particles. The supernatant is once again removed and either the wash step is repeated or the alkaline denaturation step commences. In order to release the unbiotinylated strand from the double-stranded product the beads are mixed with an alkaline denaturation solution, 0.1 M NaOH. The beads are incubated at room temperature for 10 min. which denatures the PCR product and releases the unbiotinylated product into solution. The biotinylated strand, bound to the magnetic beads is precipitated from the solution under the magnetic field and and unbiotinylated strand, now single-stranded, can optionally be transferred to a new tube with the supernatant and readied for mass spectrometric analysis.

The bound single-stranded amplified target nucleic acid can be released from the streptavidin-coated beads using one of a number of different procedures. These procedures include denaturation of biotin/streptavidin bond by heat denaturation (95° C. for 5 min.), or the use of a denaturant, such as NaOH (1 mM NaOH for 15 min. at 65° C.), and use of a secondary cleavable site, such as a disulfide linkage (100 mM DTT (dithiothreitol) for 15 min. at room temperature) or a 5' thiolated nucleotide (0.1 mM $AgNO_3$ for 15 min. at room temperature) present within the primer.

Example 4

Mass Modification of Target Nucleic Acids

Mass modification of the target nucleic acid is performed during the amplification step. One or more standard deoxynucleoside triphosphates are replaced with modified deoxynucleoside triphosphates. As an example thymidine is replaced with a 5-alkynyl-substituted-2'-deoxyuridine triphosphate. Because the modified nucleotides may not be efficient substrates for DNA polymerase it may be necessary to increase the concentration of the corresponding triphosphate by a factor of 2 to 100 over normal levels.

Example 5

Analysis of Single-Stranded Amplified Tetranucleotide Repeat Region of THO1 Gene A sample of human genomic DNA is subjected to PCR amplification with the primer pair: (SEQ ID NO:1) 5'-Biotin-GTGATTCCCATTGGCCTGT(sT)CCTC-3' and (SEQ ID NO:2) 5'-AGTGCAGGTCACAGGGAA CACAGA-3', which selectively amplify the tetranucleotide repeat region of the tyrosine hydroxylase (TH01) gene to give 90–114 bp PCR products. These PCR amplified target nucleic acids are about a factor of 2 smaller products than current commercially available primers provide. The PCR reaction is performed on a 50 μL scale using 17.5 pmol of each primer and 50–100 ng of template, with 30 3-step thermal cycles, following an initial step at 94° C. for 2 min, of 94° C. for 45 s followed by 55° C. for 30 s and then 72° C. for 30 s. A final step at 72° C. for 5 min is added to complete the reaction. The biotinylated product is then bound to streptavidin-coated magnetic beads MPG (CPG Inc., Great Neck, N.Y.) and then subjected to denaturation conditions of 0.1 M NaOH for 10 minutes. The solid-support-bound single-stranded target nucleic acid is then subjected to extensive washing with 10 mM ammonium acetate and then deionized water. The single-stranded amplified target nucleic acid is then released from the beads by cleavage of the P—S bond in the cleavable primer with 0.1 mM $AgNO_3$. After 2 μL of 100 mM dithiothreitol is added to sequester the $Ag^+$ ion, the sample is evaporated to dryness in a Speed-vac concentrator. For analysis, the sample is redissolved in 1 μL deionized $H_2O$ and is mixed with 1 μL of matrix solution consisting of 3-HPA (3-hydroxypicolinic acid) in acetonitrile:$H_2O$ 1:1. The sample is deposited onto a silicon stage, dried under a gentle flow of nitrogen and is placed into the mass spectrometer.

The experimental apparatus used for analyzing the sample amplified target nucleic acids is composed of an excitation source, a sample manipulator and a TOF mass spectrometer. The excitation source used for desorption is a Nd:YAG laser. The laser is operated at a 10 Hz repetition rate, with a 5 nanosecond pulse width. The desorption laser beam maintained at an incident angle of 45° is focused onto the sample with a 250 mm focal length AL-2 coated spherical mirror to an elliptical spot size of approximately 100 by 150 μm. A Glan-laser polarizer (Newport Corporation, Fountain Valley, Calif.) is placed in a rotation stage in the beam path for continuously variable attenuation, allowing adjustment of the polarized Nd:YAG laser energy density from below 1 $mJ/cm^2$ to 100 $mJ/cm^2$. The optimum energy density for desorption is in the range of 10 to 20 $mJ/cm^2$.

Figure 13:
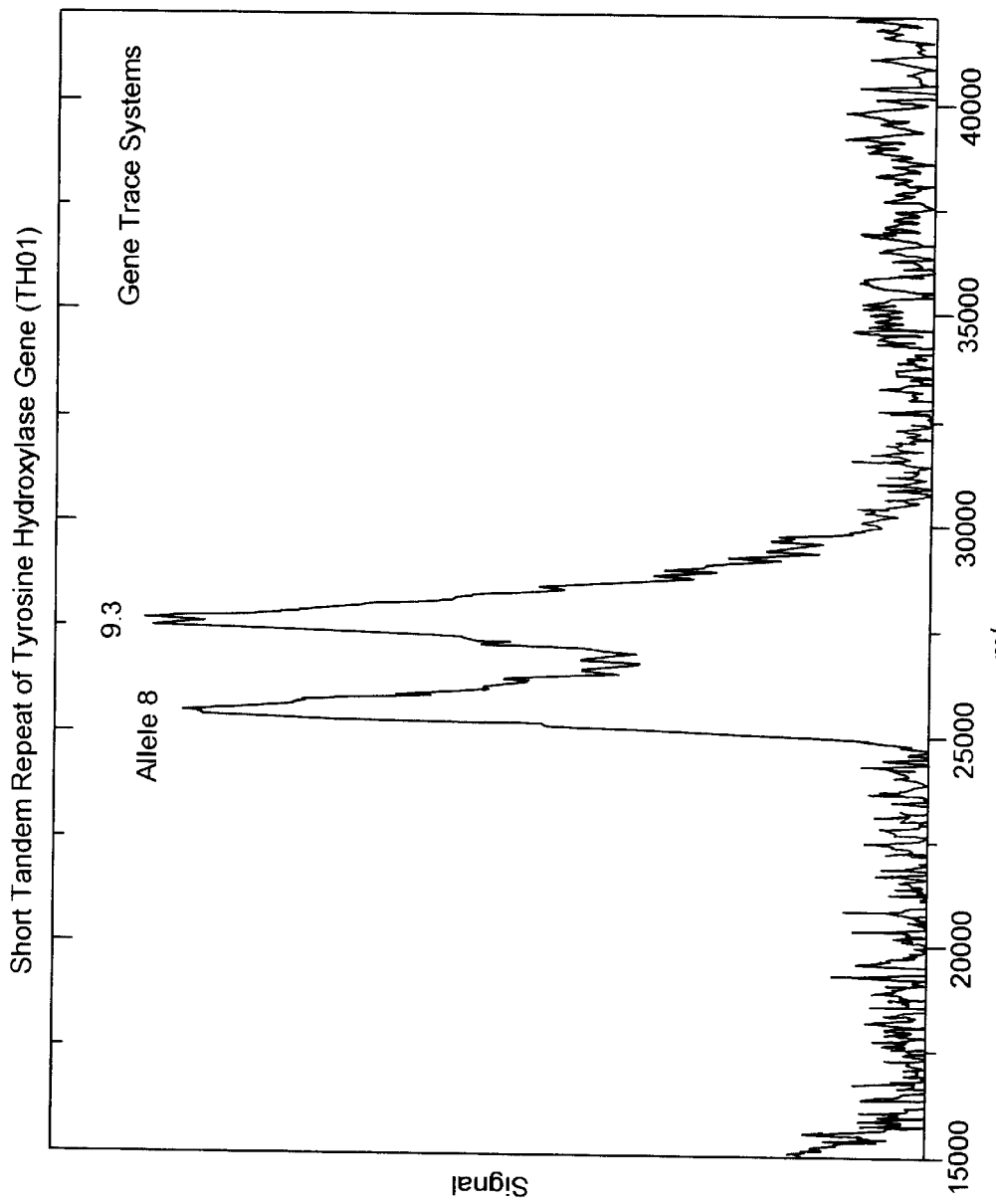
FIG. 13 is a mass spectrum of single-stranded amplified short tandem repeats from the tyrosine hydroxylase gene (TH01).

Mass spectra are recorded in positive-ion mode at room temperature. The sample region is evacuated by a 300 liter per second turbomolecular pump. The drift and detection regions are evacuated using a cryopump with nominal 1500 liter per second pumping speed. The base pressure of the chamber is $3 \times 10^{-9}$ Torr, and the normal working pressure, within about five minutes of sample introduction, is $5 \times 10^{-8}$ Torr. A total of 100 laser shots are summed to obtain a spectrum. The spectrum shown in FIG. 13 reveals two clear peaks corresponding to an 84-mer and a 91-mer, which are the expected product sizes corresponding to 8 and 9.3 repeats with one extra adenine base added to the 3'-end of each, due to the well-known property of Taq DNA polymerase to yield one-base over-extensions. The two peaks arise because the final sample, though single-stranded, derives from amplification of a heterozygous allele.

Example 6

Figure 14:
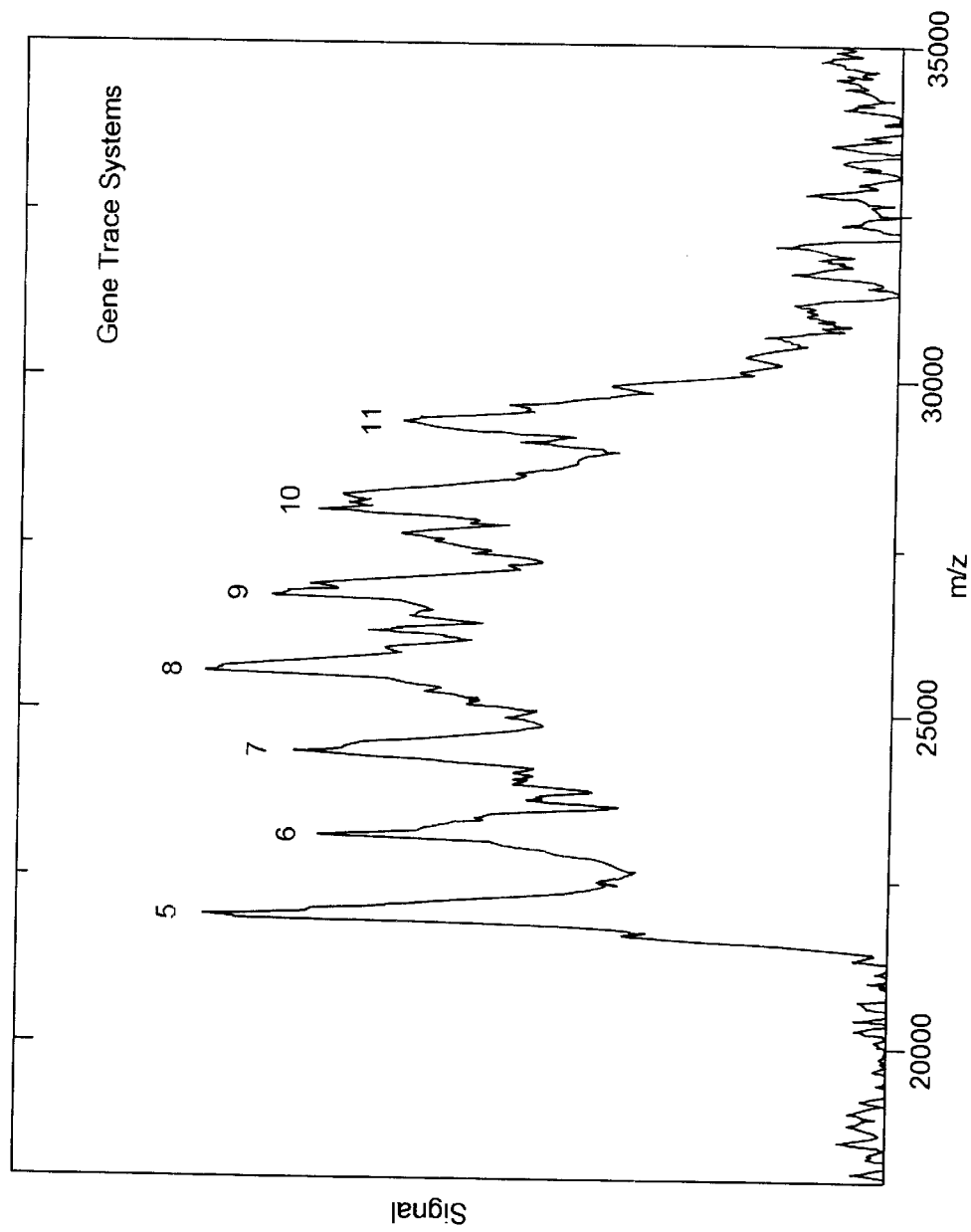
FIG. 14 is a mass spectrum of a set (ladder) of single-stranded amplified target nucleic acids, wherein the single-stranded amplified target nucleic acids ranged in length from 71 to 95 nucleotides in length.
Figure 15:
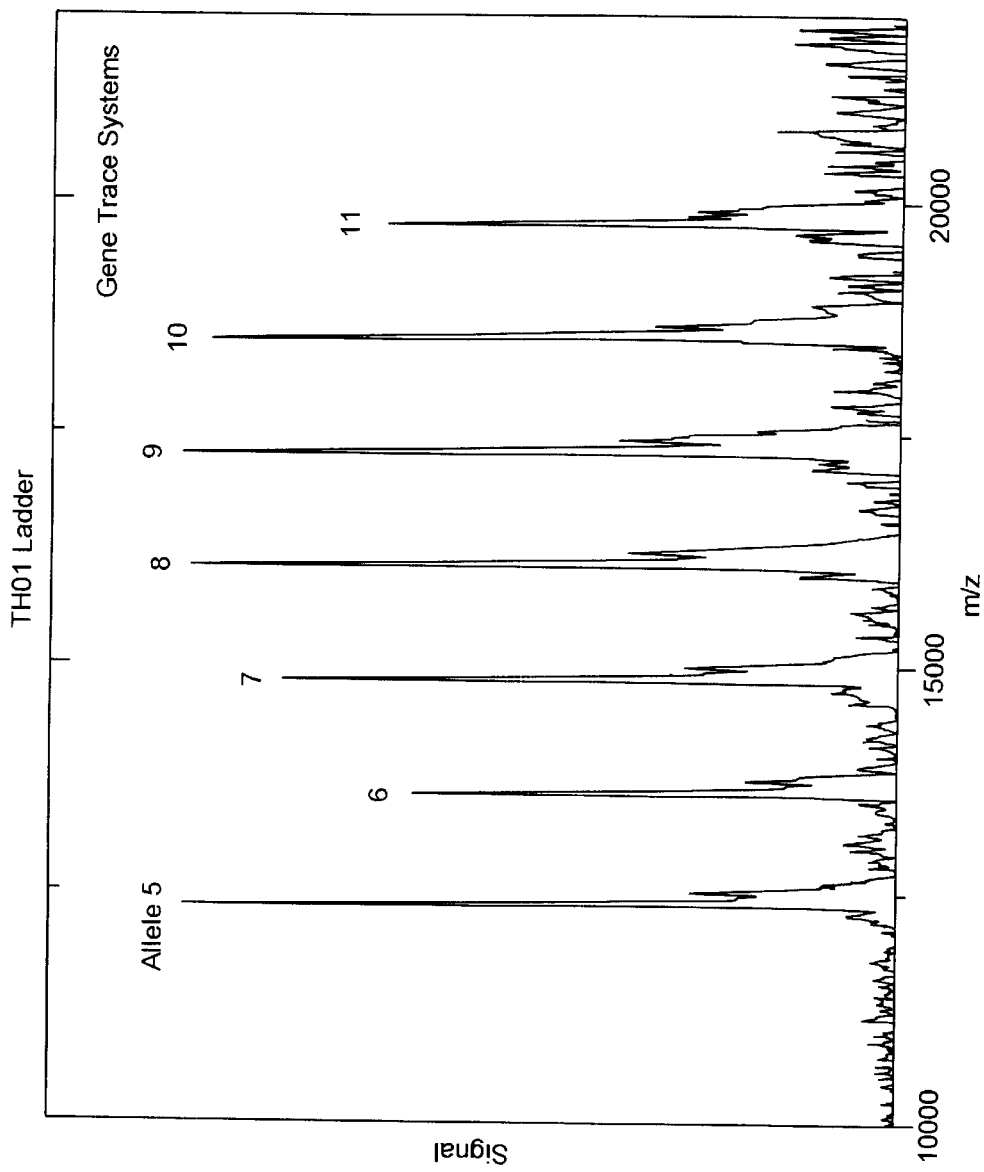
FIG. 15 is a mass spectrum of a set of single-stranded amplified target nucleic acids wherein the single-stranded amplified target nucleic acids were the same as those depicted in FIG. 14 except that the lengths of the amplified target nucleic acids had been shortened by 31 base pairs.

Comparison of Mass Spectra for Single-stranded Amplified TH01 Ladder of Nucleic Acids and for Single-stranded Amplified TH01 Ladder That Have Had Their Lengths Reduced by Endonuclease Cleavage A 1 μL sample of TH01 ladder (Promega Inc., Madison, Wis.) which contains PCR products ranging in size from 179–203 bp is reamplified in a 100 μL reaction volume according to the same amplification protocol as described above for genomic DNA to yield a ladder of products in the size range of 90–114 bp. One half of the product mixture (amplified target nucleic acids) is bound to streptavidin-coated magnetic beads, denatured, washed and cleaved from the beads as described in the previous example. The other half of the product mixture is then bound to the streptavidin-coated magnetic beads and washed. Then, 2 μL of 10× NEB Buffer 4 is added to the second half of the amplified target nucleic acids, followed by the addition of 16 μL of $H_2O$ and 20 units of Nco I restriction endonuclease (New England Biolabs, Beverly, Mass.) recognizing CCATGG. This restriction endonuclease was chosen to reduce the length of the amplified target nucleic acid because the amplified target nucleic acid contained a Nco I recognition site (in the wild type or consensus sequence) which was located in a flanking region and not in the region of interest. The mixture is incubated at 37° C. for 1 hour after which the enzyme is washed away, the amplified target nucleic acids are bound through biotinylated primers, denatured, washed and single-stranded amplified target nucleic acids are then cleaved from the beads with $AgNO_3$. The restriction enzyme-digested ladder has a size range of 40 to 64 bases as a result of the enzyme cutting 3 bp past the end of the final CATT repeat. Samples of both undigested/full-length and digested/reduced-length products are prepared for mass spectrometry analysis by reducing the volume by evaporation and adding 1 μL of 3-hydroxypicolinic acid matrix solution and allowing to dry on the sample plate. The resulting positive-ion mass spectra of the undigested and digested ladders are shown in FIGS. 14 and 15, respectively. The mass resolution of the peaks for the digested ladder (FIG. 15) is much greater than that for the undigested ladder (FIG. 14). This is due to the use of Nco I to reduce the length of the single-stranded amplified target nucleic acids that were subjected to mass spectrometric analysis.

Example 7

Mass Spectrometry Analysis

The single-stranded amplified target nucleic acid sample to be analyzed is typically mixed with an equal volume of matrix solution consisting of 0.5 M 3-hydroxypicolinic acid (3-HPA) and 50 mM diammonium hydrogen citrate. Typically, a 1 µL portion of the sample is applied to the mass spectrometer sample stage and allowed to dry under a gentle stream of nitrogen gas at room temperature. When the sample has completely dried to form crystals (typically 5 min.) the sample is inserted into the mass spectrometer for analysis. The usual analysis conditions employ the use of a Nd:YAG laser operating at 266 nm with an average pulse energy of 15 mJ/cm$^2$. An average of 100 laser shots is typically used to obtain a spectrum.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the invention and the appended claims.

regions to produce one or more reduced-length target nucleic acids, and (d) determining the masses of each of said reduced-length target nucleic acids using a mass spectrometer.

2. The method of claim 1, wherein at least one of the reduced-length target nucleic acids is single-stranded.

3. The method of claim 1, wherein at least one of the reduced-length target nucleic acids is double-stranded.

4. The method of claim 1, wherein said reducing step further comprises:

cleaving with a restriction endonuclease capable of cleaving at a cleavable site within both flanking regions.

5. The method of claim 4, wherein said restriction endonuclease is a Type IIS restriction endonuclease.

6. The method of claim 4, wherein said restriction endonuclease is a Type II restriction endonuclease.

7. The method of claim 4, wherein one or more recognition sites for said restriction endonuclease is introduced into the two flanking regions by using one or more cleavable primers each comprising said recognition sites during said amplifying step.

8. The method of claim 1, wherein said reducing step comprises treating said amplified target nucleic acid with a 5' to 3' exonuclease, wherein a cleavable primer comprising an exonuclease blocking moiety has been introduced during said amplifying step.

9. The method of claim 1, wherein said reducing step further comprises:

---

---

We claim:

1. A method of preparing one or more target nucleic acids for mass spectrometric analysis comprising:

(a) identifying one or more target nucleic acids, wherein each of said target nucleic acids comprises a region of interest and two flanking regions, (b) amplifying at least one target nucleic acid to produce at least one amplified target nucleic acid;

(c) reducing length of at least one of said target nucleic acids by cleaving off at least a portion of both flanking cleaving with a chemical capable of cleaving at a cleavable site within both flanking regions.

10. The method of claim 1, further comprising:

purifying one or more reduced-length amplified target nucleic acids.

11. The method of claim 10, wherein the one or more reduced length amplified target nucleic acid comprises a strand of interest hybridized to a complementary strand, and wherein said purifying comprises:

binding the complementary strand of a strand of interest of each of said amplified target nucleic acids to a solid support to produce a bound complementary strand, and removing at least one strand of interest from said bound complementary strand, wherein the mass of the strand of interest is determined using a mass spectrometer.

12. The method of claim 10, wherein the one or more reduced length amplified target nucleic acid comprises a strand of interest hybridized to a complementary strand, and wherein said purifying comprises:

binding one or more strand of interest to a solid support to produce a bound strand of interest, removing one or more unbound components comprising said complementary strand by washing, and releasing said bound strand of interest from said solid support, wherein the mass of the strand of interest is determined using a mass spectrometer.

13. The method of claim 12, wherein said releasing comprises cleaving a cleavable linker.

14. The method of claim 12, wherein said reducing and purifying are the same steps, comprising:

binding one or more of said amplified target nucleic acids to a solid support via a cleavable primer to produce at least one bound amplified target nucleic acid, wherein said cleavable primer has been incorporated during said amplifying step, and releasing reduced-length amplified target nucleic acids comprising cleaving at one or more cleavable sites within or near said cleavable primer.

15. The method of claim 14, wherein said cleavable primer comprises an exonuclease blocking moiety and wherein said cleaving comprises degrading said bound amplified target nucleic acids with a 5'-3' exonuclease, resulting in reduced-length amplified target nucleic acids that are single-stranded.

16. The method of claim 14, wherein said cleavable primer comprises a recognition site for a restriction endonuclease and wherein said cleaving comprises treating said bound amplified target nucleic acid with said restriction endonuclease.

17. The method of claim 10, wherein said purifying comprises:

binding a strand of interest of at least one of said amplified target nucleic acids to a solid support to produce a bound strand of interest and an unbound complementary strand, removing the unbound strand of each of said bound strands of interest from said bound strand of interest by denaturing and washing; and releasing said bound strand of interest of said amplified target nucleic acids from said solid support to form single-stranded amplified target nucleic acids, wherein the mass of the single-stranded amplified target nucleic acids is determined using a mass spectrometer.

18. The method of claim 17, wherein said bound strands of said amplified target nucleic acids each comprises a cleavable site within or adjacent to a flanking region of said amplified target nucleic acids.

19. The method of claim 18, wherein said releasing further comprises cleaving said cleavable sites.

20. The method of claim 19, wherein said cleavable sites are introduced into at least one of said amplified target nucleic acids by using a cleavable primer during said amplifying step.

21. The method of claim 19, wherein said cleaving comprises:

cleaving with a restriction endonuclease at a cleavable site within both flanking regions.

22. The method of claim 21, wherein said restriction endonuclease is a Type IIS restriction endonuclease.

23. The method of claim 21, wherein said restriction endonuclease is a Type II restriction endonuclease.

24. The method of claim 21, wherein one or more recognition sites for said restriction endonuclease are introduced into both flanking regions by using one or more cleavable primers each comprising said recognition sites during said amplifying step.

25. The method of claim 19, wherein said cleaving comprises treating said amplified target nucleic acid with a 5' to 3' exonuclease, wherein a cleavable primer comprising an exonuclease blocking moiety has been introduced during said amplifying step.

26. The method of claim 19, wherein said cleaving comprises cleaving with a chemical capable of cleaving at a cleavable site within both flanking regions.

27. The method of claim 26, wherein the cleavable site comprises a phosphorothioate linkage.

28. The method of claim 9, wherein the cleavable sites comprises a phosphorothioate linkage.

29. The method of claim 14, wherein the cleavable sites comprises a phosphorothioate linkage.

30. The method of claim 1, wherein at least one of said reduced-length amplified target nucleic acids has one or more nucleotides replaced with mass-modified nucleotides.

31. The method of claim 1, wherein said determining step further comprises utilizing internal self-calibrants to provide improved mass accuracy.

32. A method of determining the mass of one or more target nucleic acids comprising:

(a) amplifying at least one of said target nucleic acids to reproduce an amplified target nucleic acid, wherein said amplified target nucleic acid comprises a strand of interest and a complementary strand, the strand of interest comprising a region of interest and two flanking regions, wherein the complementary strand is hybridized to the strand of interest, (b) binding the strand of interest to a solid support to produce a bound strand of interest, (c) removing the complementary strand from the bound strand of interest by denaturing and washing, (d) releasing the bound strand of interest from the solid support to form a single-stranded amplified target nucleic acid, (e) reducing the length of the single-stranded amplified target nucleic acid by cleaving off at least a portion of both flanking regions, and (f) determining-the mass of said reduced-length single-stranded amplified target nucleic acid using a mass spectrometer.

33. The method of claim 32, wherein said reducing step further comprises:

cleaving with a restriction endonuclease capable of cleaving at a cleavable site within or adjacent to both flanking regions of said amplified target nucleic acids.

34. The method of claim 32, wherein said releasing step and said reducing step comprises cleaving said cleavable sites.

35. The method of claim 33, wherein said cleavable sites are introduced into said amplified target nucleic acids by using cleavable primers during said amplifying step.

36. The method of claim 34, wherein said cleaving comprises:

cleaving with a restriction endonuclease at a cleavable site within both flanking regions.

37. The method of claim 36, wherein said restriction endonuclease is a Type IIS restriction endonuclease.

38. The method of claim 36, wherein said restriction endonuclease is a Type II restriction endonuclease.

39. The method of claim 36, wherein one or more recognition sites for said restriction endonuclease is introduced into both flanking regions by using one or more cleavable primers each comprising said recognition sites during said amplifying step.

40. The method of claim 34, wherein said cleaving comprises treating said amplified target nucleic acid with a 5' to 3' exonuclease, wherein a cleavable primer comprising an exonuclease blocking moiety has been introduced during said amplifying step.

41. The method of claim 34, wherein said cleaving comprises cleaving with a chemical capable of cleaving at a cleavable site within both flanking regions.

42. The method of claim 41, wherein the cleavable site comprises a phosphorothioate linkage.

43. The method of claim 32, wherein said releasing comprises using a cleavable linker.

44. The method of claim 32, wherein said determining does not involve sequencing of said amplified target nucleic acids.

45. A method of determining the mass of a target nucleic acid which includes a region of interest and two flanking regions, which comprises:

(a) reducing the length of the target nucleic acid by removing at least a portion of both of the flanking regions;

(b) isolating the reduced-length target nucleic acid from its complementary strand; and (c) determining the mass of the isolated, reduced-length target nucleic acid by mass spectrometry.

46. The method of claim 45, wherein the target nucleic acid is single-stranded.

47. The method of claim 45, wherein the target nucleic acid is double-stranded and the isolated, reduced-length target nucleic acid comprises one of the two strands.

48. A method of determining the mass of one or more target nucleic acids comprising:

(a) identifying one or more target nucleic acids, wherein each of said target nucleic acids comprises a region of interest, at least one Type IIs restriction site, and at least two flanking regions;

(b) amplifying at least on target nucleic acid to produce at least one amplified target nucleic acid;

(c) reducing the length of at least one of said amplified target nucleic acids by cleaving off at least a portion of both flanking regions with a Type IIs restriction endonuclease to produce one or more reduced-length target nucleic acids; and (d) determining the mass of at least one of said reduced-length, target nucleic acids using a mass spectrometer.

* * * * *

UNITED STATES PATENT AND TRADEMARK OFFICE
CERTIFICATE OF CORRECTION

PATENT NO. : 6,566,055 B1  
DATED : May 20, 2003  
INVENTOR(S) : Monforte et al.

It is certified that error appears in the above-identified patent and that said Letters Patent is hereby corrected as shown below:

<u>Title page,</u>  
Item [75], Inventors, please replace "Thomas A. Shaler, Fremont CA (US)" with -- Thomas Shaler, San Francisco, CA (US) --; and please replace "Christopher H. Becker, Menlo Part, CA (US)" with -- Christopher H. Becker, Menlo Park, CA (US) --

Signed and Sealed this

Seventh Day of October, 2003

JAMES E. ROGAN  
*Director of the United States Patent and Trademark Office*

SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (20)
<223> OTHER INFORMATION: substituted thymidine
<223> OTHER INFORMATION: 5' Biotin

<400> SEQUENCE: 1
gtgattccca ttggcctgtn cctc                                          24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 2
agtgcaggtc acagggaaca caga                                          24